(12) United States Patent
Tsukamoto et al.

(10) Patent No.: US 11,752,150 B2
(45) Date of Patent: Sep. 12, 2023

(54) ANTI-TUMOR IMMUNOTHERAPY ENHANCER

(71) Applicant: Nobuo Tsukamoto, Tokyo (JP)

(72) Inventors: Nobuo Tsukamoto, Tokyo (JP); Yutaka Kawakami, Tokyo (JP)

(73) Assignee: Nobuo Tsukamoto, Tokyo (JP)

( * ) Notice: Subject to any disclaimer, the term of this patent is extended or adjusted under 35 U.S.C. 154(b) by 460 days.

(21) Appl. No.: 16/625,936

(22) PCT Filed: Jun. 29, 2018

(86) PCT No.: PCT/JP2018/024950
§ 371 (c)(1),
(2) Date: Apr. 6, 2020

(87) PCT Pub. No.: WO2019/004464
PCT Pub. Date: Jan. 3, 2019

(65) Prior Publication Data
US 2020/0383981 A1    Dec. 10, 2020

(30) Foreign Application Priority Data
Jun. 29, 2017  (JP) ................................. 2017-127973

(51) Int. Cl.
| | | |
|---|---|---|
| A61K 31/506 | (2006.01) | |
| A61P 35/00 | (2006.01) | |
| A61K 39/395 | (2006.01) | |
| C07K 16/28 | (2006.01) | |
| C12Q 1/26 | (2006.01) | |
| G01N 33/574 | (2006.01) | |
| A61K 39/00 | (2006.01) | |

(52) U.S. Cl.
CPC ...... *A61K 31/506* (2013.01); *A61K 39/39533* (2013.01); *A61P 35/00* (2018.01); *C07K 16/2818* (2013.01); *C12Q 1/26* (2013.01); *C12Y 113/11052* (2013.01); *G01N 33/574* (2013.01); *A61K 2039/505* (2013.01); *G01N 2333/90241* (2013.01); *G01N 2440/14* (2013.01); *G01N 2500/04* (2013.01); *G01N 2500/20* (2013.01)

(58) Field of Classification Search
CPC ............ A61K 31/506; A61K 39/39533; C07K 16/2818; C12Q 1/26
See application file for complete search history.

(56) References Cited

U.S. PATENT DOCUMENTS

| | | |
|---|---|---|
| 2010/0098701 A1 | 4/2010 | Jure-Kunkel et al. |
| 2012/0121604 A1 | 5/2012 | June-Kunkel et al. |
| 2012/0135001 A1 | 5/2012 | Jure-Kunkel et al. |
| 2013/0142805 A1 | 6/2013 | Jure-Kunkel et al. |
| 2014/0141024 A1 | 5/2014 | June-Kunkel et al. |

FOREIGN PATENT DOCUMENTS

JP       2012-533619 A    12/2012

OTHER PUBLICATIONS

Buettner et al., Inhibition of Src Family Kinases with Dasatinib Blocks Migration and Invasion of Human Melanoma Cells, Mol Cancer Res, 2008, 6(11), 1766-1774, Publication Date: Nov. 2008 (Year: 2008).*
Roskoski, Src protein-tyrosine kinase structure, mechanism, and small molecule inhibitors, Pharmacological Research 94(2015) 9-25, Publication Date: Feb. 3, 2015 (Year: 2015).*
Porkka et al., An open-label, phase 1b, dose-escalation study (CA180-373) of dasatinib plus nivolumab, Journal of Clinical Oncology, vol. 32, Issue 15, suppl, Meeting Abstract, 2014 ASCO annual Meeting I, Publication Date: May 20, 2014 (Year: 2014).*
Araujo et al., Dasatinib: Apotent SRC inhibitor in clinical development for the treatment of solid tumors, Cancer Treatment Review 36(2010): 492-500, Publication Year: 2010 (Year: 2010).*
Volpi et al., Allosteric modulation of metabotropic glutamate receptor 4 activates IDO1-dependent, immunoregulatory signaling in dendritic cells, Neuropharmacology, 102 (2016): 59-71, Publication Date: Oct. 30, 2015 (Year: 2015).*
Buque et al., Trial Watch—Small molecules targeting the immunological tumor mircroenvironment for cancer therapy, Oncoimmunology, vol. 5, No. 6, e1149674, Publication Date: May 23, 2016 (Year: 2016).*
Albini et al., Distinct roles of immunoreceptor tyrosine-based motifs in immunosuppressive indoleamine 2,3-dioxygenase 1, J. Cell. Mol. Med. Vol 21, No. 1, 165-176, Publication Date: Sep. 30, 2016 (Year: 2016).*
Belguise et al., "Green Tea Polyphenols Reverse Cooperation between c-Rel and CK2 that Induces the Aryl Hydrocarbon Receptor, Slug, and an Invasive Phenotype," Cancer Research, 67: 11742-11750 (2007).
Brochez et al., "The rationale of indoleamine 2,3-dioxygenase inhibition for cancer therapy," European Journal of Dancer, 76: 167-182 (2017).

(Continued)

*Primary Examiner* — Peter J Reddig
*Assistant Examiner* — Cheng Lu
(74) *Attorney, Agent, or Firm* — Morgan, Lewis & Bockius LLP

(57) ABSTRACT

The disclosure provides a composition for inhibiting the growth and/or invasion of tumor cells, an enhancer of an anti-tumor effect of a drug for the purpose of removing immunosuppression caused by cancer, or the like, which is characterized by being used for a specific subject.

10 Claims, 12 Drawing Sheets

Specification includes a Sequence Listing.

(56) References Cited

OTHER PUBLICATIONS

Kulkarni et al., "Combining Immune Checkpoint Inhibitors and Kinase-lnhibiting Supramolecular Therapeutics for Enhanced Anticancer Efficacy," American Chemical Society Nano, 10: 9227-9242 (2016).

Reddy et al., "Influences of BRAF Inhibitors on the Immune Microenvironment and the Rationale for Combined Molecular and Immune Targeted Therapy," Current Oncology Reports, 18:42 (2016).

International Search Report issued in corresponding International Patent Application No. PCT/JP2018/024950 dated Aug. 14, 2018.

Liu et al., "Selective inhibition of IDO1 effectively regulates mediators of antitumor immunity," Blood, 115 (17): 3520-3530 (2010).

Office Action issued in corresponding Japanese Patent Application No. 2019-527085 dated Feb. 20, 2023.

Hekim et al., "Dasatinib Changes Immune Cell Profiles Concomitant with Reduced Tumor Growth in Several Murine Solid Tumor Models," Cancer Immunology Research, 5 (2): 157-169 (2017).

Pallotta et al., "Indoleamine 2,3-dioxygenase is a signaling protein in long-term tolerance by dendritic cells," Nature Immunology, 12 (9): 870-878 (2011).

Coletti et al., "Advances in indoleamine 2,3-dioxygenase 1 medicinal chemistry," Med Chem Commun, 8: 1378-1392 (2017).

Notice of Reasons for Refusal issued in corresponding Japanese Patent Application No. 2019-527085 dated Jul. 4, 2022.

\* cited by examiner

ANTI-TUMOR IMMUNOTHERAPY ENHANCER

SEQUENCE LISTING SUBMISSION VIA EFS-WEB

A computer readable text file, entitled "SequenceListing.txt," created on or about Dec. 23, 2019 with a file size of about 15 kb contains the sequence listing for this application and is hereby incorporated by reference in its entirety.

TECHNICAL FIELD

The present invention relates to an anti-tumor immunotherapy and/or an anti-tumor immunotherapy enhancer etc.

BACKGROUND ART

Indoleamine 2,3-dioxygenase (IDO) is an enzyme that catalyzes the conversion of L-tryptophan to N-formylkynurenine and is a rate-limiting enzyme that catalyzes the first step of tryptophan metabolisms in the kynurenine pathway. Similarly, Tryptophan 2,3-dioxygenase (TDO) is known as an enzyme that catalyzes the conversion of L-tryptophan to N-formylkynurenine.

It is known that when IDO or TDO is expressed in tumor tissues, etc., since it metabolizes tryptophan (Trp), T cells become unable to utilize Trp, and also known that kynurenine produced from Trp catalyzed by IDO or TDO is released from cancer cells and activates the aryl hydrocarbon receptor (AhR) of surrounding immune cells and converts the immune cells suppressive. Therefore, drugs (epacadostat, indoximod, etc.) that suppress the enzyme activity of IDO or TDO to metabolize Trp have been developed, and in addition to monotherapy, combination therapies with immune checkpoint inhibitors have been clinically applied (Non-Patent Document 1).

Due to the effect of immune checkpoint inhibitors on anti-tumor immunity, immune checkpoint inhibitors have been attracting attention as an unprecedented cancer treatment, but patients who actually show effective responses are limited, and even in effective cases part of the patients are not completely cured, thus further development of anti-tumor immunotherapy is required. For example, various attempts have been made to use an immune checkpoint inhibitor and a BRAF/MEK kinase inhibitor in combination (Non-Patent Document 2), and it has been reported that some of such combinations enhance the anti-tumor effect in melanoma (Non-Patent Document 3), however, development of useful anti-tumor immunotherapy is still expected.

PRIOR ART DOCUMENTS

Non-Patent Documents

Non-patent document 1: L. Brochez et al., Eur J Cancer 76, 2017, pp. 167-182
Non-patent document 2: Sangeetha M. Reddy et al. Curr Oncol Rep, 2016, 18(7), pp 42-50
Non-patent document 3: Ashish Kulkarni et al., ACS NANO, 2016, 10(10), pp. 9227-9242)

SUMMARY OF INVENTION

Problem to be Solved by Invention

However, there is still a need for further development of anti-tumor immunotherapy. In particular, the demand for personalized medical treatment for a specific treatment target patient is particularly strong in the field of cancer treatment, and it is necessary to select a specific subject and then use a particularly useful drug for the subject.

One aspect of the present invention is intended to provide a composition for inhibiting the growth and/or invasion of a tumor cell, an enhancer of anti-tumor effect of a drug for the purpose of removing immunosuppression caused by cancer, or the like, which is used for a specific subject. Another aspect of the present invention is intended to provide a method for specifying such a subject (a method for acquiring data for specifying such a subject).

Means of Solving Problem

The present inventors have conducted intensive studies and newly found that, in some tumor cells in tumor tissues, inhibiting phosphorylation at a specific site(s) of IDO1 enhances an anti-tumor immune response and exhibits an anti-tumor effect. In addition, the present inventors have newly found that inhibition of phosphorylation at a specific site(s) of IDO1 is particularly useful in combination with treatment with a drug for the purpose of removing immunosuppression caused by cancer. The present invention is based on such new findings.

One embodiment of the present invention relates to the following.

[1] A composition for inhibiting the growth and/or invasion of a tumor cell, wherein the composition includes a phosphorylation inhibitor or a dephosphorylation agent against phosphorylation of:

a tyrosine residue(s) at the 111-th position and/or the 249-th position of human IDO1; or a tyrosine residue(s) of non-human IDO1 at a position(s) corresponding to the 111-th position and/or the 249-th position of human IDO1 and wherein the composition is used for a tumor cell in which the tyrosine residue(s) is/are phosphorylated or used for a subject who carries the tumor cell.

[2] The composition according to [1] described above, wherein the phosphorylation inhibitor or the dephosphorylation agent is a Src inhibitor or an inhibitor against a factor which increases phosphorylation activity of Src on the tyrosine residue(s).

[3] The composition according to [1] or [2] described above, wherein the phosphorylation inhibitor or the dephosphorylation agent is a Src inhibitor selected from a group consisting of dasatinib, bosutinib, saracatinib, ponatinib, ilorasertib, N-benzyl-2-(5-(4-(2-morpholinoethoxy)phenyl)pyridin-2-yl)acetamide, 4-amino-5-(4-chlorophenyl)-7-(tert-butyl)pyrazolo-[3,4-d]pyrimidine, 4-amino-5-(4-methylphenyl)-7-(tert-butyl)pyrazolo-[3,4-d]pyrimidine, 4-(4'-phenoxyanilino)-6,7-dimethoxyquinazoline, 2-((3,5-di-tert-Butyl-4-hydroxyphenyl)-methylene)-4-cyclopentene-1,3-dione, 4-N-(5-cyclopropyl-1H-pyrazol-3-yl)-6-(4-methylpiperazin-1-yl)-2-N-[(3-propan-2-yl-1,2-oxazol-5-yl)methyl]pyrimidine-2,4-diamine, [7-(2,6-dichlorophenyl)-5-methyl-benzo[1,2,4]triazin-3-yl]-[4-(2-pyrrolidin-1-yl-ethoxy)-phenyl]-amine, [7-(2,6-dichlorophenyl)-5-methyl-benzo[1,2,4]triazin-3-yl]-{4-[2-(1-oxy-pyrrolidin-1-yl)ethoxy]-phenyl}-amine, and rebastinib, and salts, hydrates, and solvates thereof.

[4] The composition according to any one of [1] to [3] described above, characterized in that the composition is used in combination with a drug for the purpose of removing immunosuppression caused by cancer.

[5] The composition according to [4] described above, wherein the drug for the purpose of removing immunosuppression caused by cancer includes anti-PD-1 antibody or anti-PD-L1 antibody.

[6] An enhancer of anti-tumor effect of a drug for the purpose of removing immunosuppression caused by cancer, wherein the enhancer of anti-tumor effect includes a phosphorylation inhibitor or a dephosphorylation agent against phosphorylation of:
  a tyrosine residue(s) at the 111-th position and/or the 249-th position of human IDO1; or
  a tyrosine residue(s) of non-human IDO1 at a position(s) corresponding to the 111-th position and/or the 249-th position of human IDO1, and
  wherein the enhancer of anti-tumor effect is used for a tumor cell in which the tyrosine residue(s) is/are phosphorylated or used for a subject who carries the tumor cell.

[7] The enhancer of anti-tumor effect according to [6] described above, wherein the phosphorylation inhibitor or the dephosphorylation agent is a Src inhibitor or an inhibitor against a factor which increases phosphorylation activity of Src on the tyrosine residue(s).

[8] The enhancer of anti-tumor effect according to [6] or [7] described above, wherein the phosphorylation inhibitor or the dephosphorylation agent is a Src inhibitor selected from a group consisting of dasatinib, bosutinib, saracatinib, ponatinib, ilorasertib, N-benzyl-2-(5-(4-(2-morpholinoethoxy)phenyl)pyridin-2-yl)acetamide, 4-amino-5-(4-chlorophenyl)-7-(tert-butyl)pyrazolo-[3,4-d]pyrimidine, 4-amino-5-(4-methylphenyl)-7-(tert-butyl)pyrazolo-[3,4-d]pyrimidine, 4-(4'-phenoxyanilino)-6,7-dimethoxyquinazoline, 2-((3,5-di-tert-Butyl-4-hydroxyphenyl)-methylene)-4-cyclopentene-1,3-dione, 4-N-(5-cyclopropyl-1H-pyrazol-3-yl)-6-(4-methylpiperazin-1-yl)-2-N-[(3-propan-2-yl-1,2-oxazol-5-yl)methyl]pyrimidine-2,4-diamine, [7-(2,6-dichlorophenyl)-5-methyl-benzo[1,2,4]triazin-3-yl]-[4-(2-pyrrolidin-1-yl-ethoxy)-phenyl]-amine, [7-(2,6-dichlorophenyl)-5-methyl-benzo[1,2,4]triazin-3-yl]-{4-[2-(1-oxy-pyrrolidin-1-yl)-ethoxy]-phenyl}-amine, and rebastinib, and salts, hydrates, and solvates thereof.

[9] The enhancer of anti-tumor effect according to any one of [6] to [8] described above, characterized in that the enhancer is used in combination with a drug for the purpose of removing immunosuppression caused by cancer.

[10] The enhancer of anti-tumor effect according to any one of [6] to [9] described above, wherein the drug for the purpose of removing immunosuppression caused by cancer includes anti-PD-1 antibody or anti-PD-L1 antibody.

[11] A method for obtaining data to identify a subject suitable for administration of a composition for inhibiting the growth and/or invasion of a tumor cell or an enhancer of anti-tumor effect of a drug for the purpose of removing immunosuppression caused by cancer, wherein the method includes:
  detecting, in a tumor cell obtained from the subject, phosphorylation of:
    a tyrosine residue(s) at the 111-th position and/or the 249-th position of human IDO1; or
    a tyrosine residue(s) of non-human IDO1 at a position(s) corresponding to the 111-th position and/or the 249-th position of human IDO1, and
  wherein the composition or the enhancer of anti-tumor effect includes a phosphorylation inhibitor or a dephosphorylation agent against phosphorylation of the tyrosine residue(s).

[12] An antibody to identify a subject suitable for administration of a composition for inhibiting the growth and/or invasion of a tumor cell or an enhancer of anti-tumor effect of a drug for the purpose of removing immunosuppression caused by cancer,
  wherein the antibody detects, in a tumor cell obtained from the subject, phosphorylation of:
    a tyrosine residue(s) at the 111-th position and/or the 249-th position of human IDO1; or
    a tyrosine residue(s) of non-human IDO1 at a position(s) corresponding to the 111-th position and/or the 249-th position of human IDO1, and
  wherein the composition or the enhancer of anti-tumor effect includes a phosphorylation inhibitor or a dephosphorylation agent against phosphorylation of the tyrosine residue(s).

[13] A method for screening a candidate substance for a composition for inhibiting the growth and/or invasion of a tumor cell or for an enhancer of anti-tumor effect of a drug for the purpose of removing immunosuppression caused by cancer, wherein the method includes:
  ex vivo measuring inhibition activity or dephosphorylation activity of a test substance against phosphorylation of:
    a tyrosine residue(s) at the 111-th position and/or the 249-th position of human IDO1; or
    a tyrosine residue(s) of non-human IDO1 at a position(s) corresponding to the 111-th position and/or the 249-th position of human IDO1; and
  selecting the candidate substance based on the measured inhibition activity or dephosphorylation activity of the test substance.

[14] A method for screening a candidate substance to suppress expression of Slug gene induced by phosphorylation of IDO1 or synthesis of Slug induced by phosphorylation of IDO1, wherein the method includes:
  ex vivo measuring inhibition activity or dephosphorylation activity of a test substance against phosphorylation of:
    a tyrosine residue(s) at the 111-th position and/or the 249-th position of human IDO1; or
    a tyrosine residue(s) of non-human IDO1 at a position corresponding to the 111-th position and/or the 249-th position of human IDO1; and
  selecting the candidate substance based on the measured inhibition activity or dephosphorylation activity of the test substance.

[15] A method for screening a candidate substance for a composition for inhibiting the growth and/or invasion of a tumor cell or for an enhancer of anti-tumor effect of a drug for the purpose of removing immunosuppression caused by cancer, wherein the method includes:
  ex vivo measuring inhibition activity by a test substance against Src or Slug, inhibition activity by a test substance against a factor which activates Src or Slug, synthesis of Src or Slug by a test substance, or expression of Src gene or Slug gene by a test substance; and
  selecting the candidate substance based on the measured inhibition activity by the test substance against Src or Slug, the measured inhibition activity by the test substance against a factor which activates Src or Slug, measured synthesis inhibition of Src or Slug by the test substance, or measured expression inhibition of Src gene or Slug gene by the test substance, and
  wherein the composition or the enhancer of anti-tumor effect is used for a tumor cell in which a tyrosine residue(s) at the 111-th position and/or the 249-th position of human IDO1, or a tyrosine residue(s) of non-human IDO1 at a position(s) corresponding to the 111-th position and/or the 249-th position of human IDO1 is/are phosphorylated, or used for a subject who carries the tumor cell.

[16] A method for screening a candidate substance for inhibiting expression of Slug gene or inhibiting synthesis of Slug, wherein the method includes:

ex vivo measuring Slug inhibition activity by a test substance, inhibition activity against a factor which activates Slug by a test substance, expression of Slug gene by a test substance, or synthesis of Slug by a test substance, in a cell in which a tyrosine residue(s) at the 111-th position and/or the 249-th position of human IDO1, or a tyrosine residue(s) of non-human IDO1 at a position(s) corresponding to the 111-th position and/or the 249-th position of human IDO1 is/are phosphorylated, and/or in a cell in which AhR is activated; and selecting the candidate substance based on the measured Slug inhibition activity by the test substance, the inhibition activity against a factor which activates Slug by the test substance, measured expression inhibition of Slug gene by the test substance, or measured synthesis inhibition of Slug by the test substance.

[17] A composition for inhibiting the growth and/or invasion of a tumor cell including a Src inhibitor and a drug for the purpose of removing immunosuppression caused by cancer.

[18] A composition for inhibiting the growth and/or invasion of a tumor cell including a Src inhibitor, wherein the composition is used in combination with a drug for the purpose of removing immunosuppression caused by cancer.

[19] The composition according to [17] or [18] described above, wherein the Src inhibitor is a phosphorylation inhibitor against phosphorylation of:

a tyrosine residue(s) at the 111-th position and/or the 249-th position of human IDO1; or a tyrosine residue(s) of non-human IDO1 at a position(s) corresponding to the 111-th position and/or the 249-th position of human IDO1.

[20] The composition according to any one of [17] to [19] described above, wherein the tumor cell is from a solid tumor.

Effect of Invention

According to one embodiment of the present invention, an anti-tumor effect can be exerted on a specific tumor cell. Here, the anti-tumor effect may include inhibiting the growth of a tumor cell and/or inhibiting invasion of a tumor cell, and/or shrinking a tumor.

According to one embodiment of the present invention, a beneficial anti-tumor effect may be achieved in combination with treatment with a drug for the purpose of removing immunosuppression caused by cancer.

In one embodiment of the present invention, a particular subject suitable for a particular cancer treatment may be identified.

In one embodiment of the present invention, a candidate substance useful for treating cancer may be screened.

DESCRIPTION OF EMBODIMENTS

Figure 1:
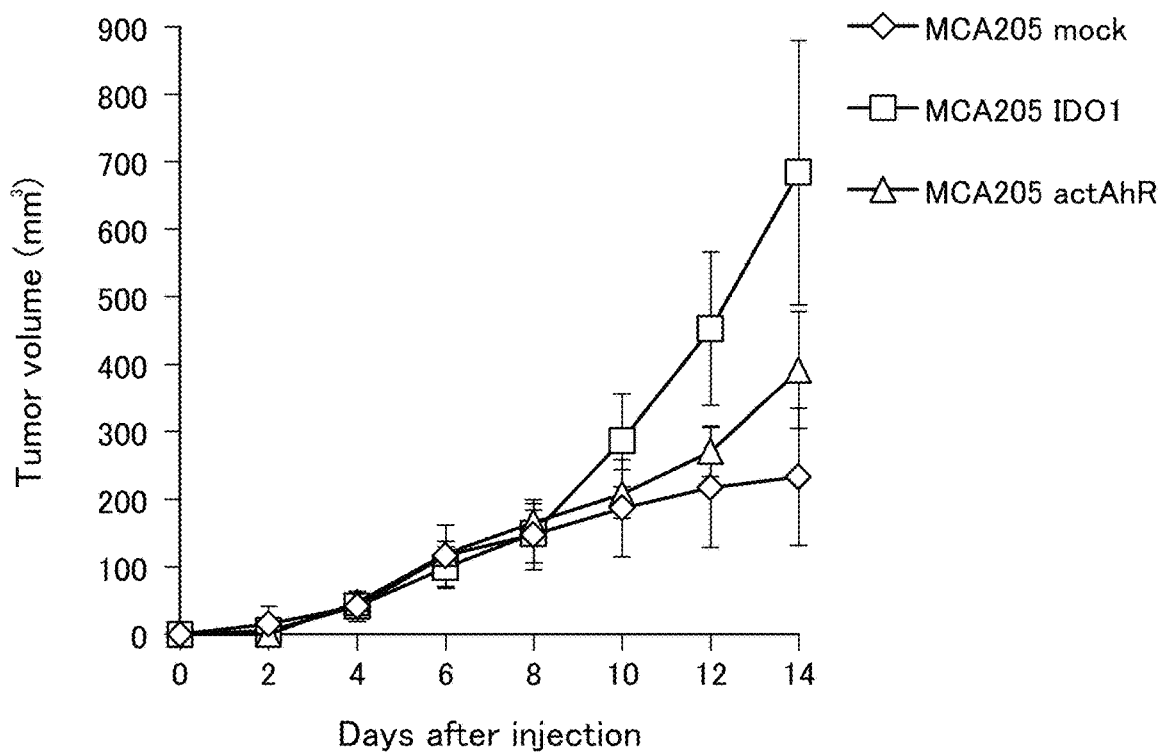
FIG. 1 is a graph showing an increase in tumor volume in C57BL/6 mice implanted with mouse cancer cells MCA205. MCA205 mock represents MCA205 transfected with an empty vector without gene insertion. MCA205 IDO1 represents MCA205 in which a wild-type mouse IDO1 gene was transfected and constitutively expressed. MCA205 act-AhR represents MCA205 in which a constitutively active mouse AhR gene was transfected and constitutively expressed.

Hereinafter, the present invention is described in detail.

One embodiment of the present invention relates to a composition for inhibiting the growth and/or invasion of tumor cells.

A composition for inhibiting the growth and/or invasion of a tumor cell of the present invention includes a phosphorylation inhibitor or a dephosphorylation agent against phosphorylation of a specific tyrosine residue(s) of IDO1. In addition, a composition for inhibiting the growth and/or invasion of a tumor cell of the present invention is used for a tumor cell in which a specific tyrosine residue(s) of IDO1 is/are phosphorylated or a subject who carries a tumor cell in which a specific tyrosine residue(s) of IDO1 is/are phosphorylated.

One embodiment of the present invention relates to an enhancer of anti-tumor effect of a drug for the purpose of removing immunosuppression caused by cancer.

An enhancer of anti-tumor effect of a drug for the purpose of removing immunosuppression caused by cancer of the present invention includes a phosphorylation inhibitor or a dephosphorylation agent against phosphorylation of a specific tyrosine residue(s) of IDO1. Further, an enhancer of anti-tumor effect of a drug for the purpose of removing immunosuppression caused by cancer of the present invention is used for a tumor cell in which a specific tyrosine residue(s) of IDO1 is/are phosphorylated or used for a subject who carries a tumor cell in which a specific tyrosine residue(s) of IDO1 is/are phosphorylated.

One embodiment of the present invention relates to a composition for inhibiting the growth and/or invasion of a tumor cell, including a Src inhibitor and a drug for the purpose of removing immunosuppression caused by cancer.

One embodiment of the present invention relates to a composition for inhibiting the growth and/or invasion of a tumor cell, including a Src inhibitor, which is used in combination with a drug for the purpose of removing immunosuppression caused by cancer.

As used herein, "tumor cell" refers to a cell(s) or a cell population(s) that proliferates abnormally, and includes benign tumors and malignant tumors. Tumor cells, also simply referred to as tumors, include solid tumors and hematological tumors. Tumor cells (tumors) may be present in organs such as, for example, lung, stomach, esophagus, liver, pancreas, intestine, kidney, spleen, genitalia, urinary organs, brain, nerves, bone marrow, and lymph nodes.

Malignant tumors are also commonly referred to as cancers. Therefore, a composition for inhibiting the growth and/or invasion of a tumor cell of the present invention and an enhancer of anti-tumor effect of a drug for the purpose of removing immunosuppression caused by cancer of the present invention may be used for treating cancer. Here, cancer is used in a broad sense including carcinomas, sarcomas, and hematological malignancies (hematopoietic tumors). A composition for inhibiting the growth and/or invasion of a tumor cell of the present invention and an enhancer of anti-tumor effect of drug for the purpose of removing immunosuppression caused by cancer of the present invention may be used for treatment of cancer, for example, lung cancer, gastric cancer, esophageal cancer, liver cancer, biliary tract cancer, pancreatic cancer, colon cancer, renal cancer, bladder cancer, prostate cancer, testicular cancer, uterine cancer, ovarian cancer, breast cancer, skin cancer, laryngeal cancer, brain tumor, neuroblastoma, colorectal cancer, melanoma, head and neck cancer, bone and soft tissue tumor, thyroid cancer, fibrosarcoma, dermal fibrosarcoma, liposarcoma, myosarcoma, hemangiosarcoma, Kaposi's sarcoma, lymphatic sarcoma, osteosarcoma, leukemia, lymphoma, and myeloma, but not limited thereto.

Since IDO1 expressed in a stromal cell of tumor tissue also metabolizes tryptophan and suppresses anti-tumor immunity, a composition for inhibiting the growth and/or invasion of a tumor cell of the present invention, and an enhancer of anti-tumor effect of a drug for the purpose of removing immunosuppression caused by cancer of the present invention may be used for a subject in which phosphorylation of a specific tyrosine residue(s) described herein is observed in IDO1 expressed in a stromal cell.

A composition for inhibiting the growth and/or invasion of a tumor cell of the present invention, and an enhancer of anti-tumor effect of a drug for the purpose of removing immunosuppression caused by cancer of the present invention may exert an anti-tumor effect on a tumor cell in which a specific tyrosine residue(s) of IDO1 is/are phosphorylated.

In the case of a solid tumor, the anti-tumor effect may be evaluated by inhibiting the growth of a tumor cell, inhibiting invasion of a tumor cell, or reducing the size of a tumor. In the case of a liquid tumor, the anti-tumor effect may be evaluated using the decrease in the number of tumor cells in blood as an index.

A specific tyrosine residue(s) of IDO1 is a tyrosine residue(s) at the 111-th position and/or the 249-th position in the case of human IDO1 (SEQ ID NO: 1), and a tyrosine residue(s) at a position(s) corresponding to the 111-th position and/or the 249-th position of human IDO1 in the case of non-human IDO1. A tyrosine residue(s) of non-human IDO1 at a position(s) corresponding to the 111-th position and/or the 249-th position of human IDO1 varies in positions in each animal. For example, in mouse IDO1 (SEQ ID NO: 2), tyrosine residue at the 115-th position corresponds to tyrosine residue at the 111-th position of human IDO1 and tyrosine residue at the 253-th position corresponds to tyrosine residue at the 249-th position of human IDO1.

IDO1 has two immunoreceptor tyrosine-based inhibitory motifs (ITIMs). The site where the tyrosine residue at position 111 of human IDO1 exists is called ITIM1, and the site where the tyrosine residue at position 249 of human IDO1 is called ITIM2. ITIM1 and ITIM2 are thought to have similar functions.

The present inventors have found that phosphorylation of a tyrosine residue(s) in a tumor cell at the 111-th position and/or the 249-th position of human IDO1 or a tyrosine residue(s) of non-human IDO1 at a position(s) corresponding to the 111-th position and/or the 249-th position of human IDO1 is involved in the suppression of anti-tumor immunity, the growth of the tumor cell, and the like. In addition, the present inventors have found that in a tumor cell, inhibition of phosphorylation of a tyrosine residue(s) at the 111-th position and/or the 249-th position of human IDO1 or a tyrosine residue(s) of non-human IDO1 at a position(s) corresponding to the 111-th position and/or the 249-th position of human IDO1 results in the exertion of an anti-tumor effect through enhancement of anti-tumor immune response, and also results in significant reduction of the amount of IDO1 in the tumor cell.

Therefore, a composition for inhibiting the growth and/or invasion of a tumor cell of the present invention and an enhancer of anti-tumor effect of a drug for the purpose of removing immunosuppression caused by cancer of the present invention are characterized by including a phosphorylation inhibitor or a dephosphorylation agent against phosphorylation of a tyrosine residue(s) at the 111-th position and/or the 249-th position of human IDO1 or a tyrosine residue(s) of non-human IDO1 at a position(s) corresponding to the 111-th position and/or the 249-th position of human IDO1. Preferably, a composition for inhibiting the growth and/or invasion of a tumor cell of the present invention and an enhancer of anti-tumor effect of a drug for the purpose of removing immunosuppression caused by cancer of the present invention include a phosphorylation inhibitor or a dephosphorylation agent against phosphorylation of a tyrosine residue at the 249-th position of human IDO1 or a tyrosine residue of non-human IDO1 at a position(s) corresponding to the 249-th position of human IDO1.

Examples of a phosphorylation inhibitor or a dephosphorylation agent against phosphorylation of a tyrosine residue(s) at the 111-th position and/or the 249-th position of human IDO1 or a tyrosine residue(s) of non-human IDO1 at a position(s) corresponding to the 111-th position and/or the 249-th position of human IDO1 includes, for example, but are not limited to, a Src inhibitor or an inhibitor against a factor which increases phosphorylation activity of Src on the tyrosine residue(s).

Examples of a Src inhibitor include compounds and antibodies that inhibit the action of the kinase Src, and compounds and nucleic acids that inhibit the expression of the Src gene. As a specific Src inhibitor, those known to have a Src inhibitory activity may be used based on literatures such as Lauren N. Puls et al., The Oncologist 2011; 16: 566-578 and others, and the knowledge of a person skilled in the art. For example, Src inhibitors include: dasatinib, bosutinib, saracatinib, ponatinib, ilorasertib, N-benzyl-2-(5-(4-(2-morpholinoethoxy)phenyl)pyridin-2-yl)acetamide (KX2-391; CAS number: 897016-82-9), 4-amino-5-(4-chlorophenyl-7-(tert-butyl)pyrazolo-[3,4-d]pyrimidine (PP2; CAS number: 172889-27-9), 4-amino-5-(4-methylphenyl)-7-(tert-butyl)pyrazolo-[3,4-d]pyrimidine (PP1; CAS number: 172889-26-8), 4-(4'-phenoxyanilino)-6,7-dimethoxyquinazoline (Src Kinase Inhibitor I; CAS number: 179248-59-0), 2((3,5-di-tert-Butyl-4-hydroxyphenyl)-methylene)-4-cyclopentene-1,3-dione (TX-1123; CAS number: 157397-06-3), 4-N-(5-cyclopropyl-1H-pyrazol-3-yl)-6-(4-methylpiperazin-1-yl)-2-N-[(3-propan-2-yl-1,2-oxazol-5-yl)methyl]pyrimidine-2,4-diamine (XL-228; CAS number: 898280-07-4), [7-(2,6-dichloro-phenyl)-5-methyl-benzo[1,2,4]triazin-3-yl]-[4-(2-pyrrolidin-1-yl-ethoxy)-phenyl]-amine (TG100435), [7-(2,6-dichloro-phenyl)-5-methyl-benzo[1,2,4]triazin-3-yl]-{4-[2-(1-oxy-pyrrolidin-1-yl)-ethoxy]-phenyl}-amine (TG100855), and rebastinib (DCC2036), and salts, hydrates, and solvates thereof, but are not limited thereto.

The salt, hydrate and solvate are not particularly limited, but may be appropriately selected as long as they are pharmaceutically acceptable. Pharmaceutically acceptable salts include, but are not particularly limited to, for example, inorganic acid salts such as hydrochloride, hydrobromide, sulfate, nitrate and phosphate; organic acid salts such as acetate, succinate, fumarate, maleate, salicylate, tartrate, citrate, oxalate, lactate, malate, stearate, benzoate, methanesulfonate, and p-toluenesulfonate; inorganic base salts such as alkali metal salts (sodium salts and potassium salts, etc.), alkaline earth metal salts (calcium salts and magnesium salts, etc.) and ammonium salts; organic base salts such as diethylamine salts; acidic amino acid salts such as aspartate and glutamate; and basic amino acid salts such as arginine salts, lysine salts and ornithine salts.

An inhibitor of a factor that enhances the specific tyrosine phosphorylation activity of Src also includes an inhibitor of a factor that enhances the activation of Src and an inhibitor of a factor that activates the expression of Src gene. Examples of an inhibitor of a factor that enhances the specific tyrosine phosphorylation activity of Src include a FAK inhibitor etc. For example, specific FAK inhibitors include 1,2,4,5-benzenetetraamine tetrahydrochloride (Y15; CAS number: 4506-66-5), defactinib, 6-[4-(3-methylsulfonylbenzylamino)-5-trifluoromethylpyrimidin-2-ylamino]-3,4-dihydro-1H-quinolin-2-one (PF-573228; CAS number: 869288-64-2) and 2-[[2-(2-methoxy-4-morpholin-4-ylanilino)-5-(trifluoromethyl)pyridin-4-yl]amino]-N-methylbenzamide (PND-1186; CAS number: 1061353-68-1), PF-00562271 (CAS number: 939791-38-5), and salts, hydrates, and solvates thereof, but are not limited thereto.

The salt, hydrate and solvate are not particularly limited, but may be appropriately selected as long as they are pharmaceutically acceptable. Pharmaceutically acceptable salts include those exemplified above.

In one embodiment of the present invention, a composition for inhibiting the growth and/or invasion of a tumor cell of the present invention is used in combination with a drug for the purpose of removing immunosuppression caused by cancer.

In one embodiment of the present invention, an enhancer of anti-tumor effect of a drug for the purpose of removing immunosuppression caused by cancer of the present invention is used in combination with a drug for the purpose of removing immunosuppression caused by cancer.

When used in combination with such a drug for the purpose of removing immunosuppression caused by cancer, an excellent anti-tumor effect may be exerted, and the anti-tumor effect may be synergistic. In particular, dasatinib, bostinib and ponatinib, which are Src inhibitors, at the time of filing the present application, are used as a medicine for treating chronic myelogenous leukemia and relapsed or refractory Philadelphia chromosome positive acute lymphocytic leukemia. On the other hand, it is surprising that a composition for inhibiting the growth and/or invasion of a tumor cell of the present invention and an enhancer of anti-tumor effect of a drug for the purpose of removing immunosuppression caused by cancer of the present invention are also useful for solid tumors (solid tumors in which the above specific tyrosine residue(s) of IDO1 is/are phosphorylated). Furthermore, it is very surprising that use of the composition or the enhancer of anti-tumor effect in combination with a drug for the purpose of removing immunosuppression caused by cancer enhances the anti-tumor effect against solid tumors (solid tumors in which the above specific tyrosine residue(s) of IDO1 is/are phosphorylated), and the enhancement of the anti-tumor effect may be synergistic.

A composition for inhibiting the growth and/or invasion of a tumor cell of the present invention, and an enhancer of anti-tumor effect of a drug for the purpose of removing immunosuppression caused by cancer of the present invention are not prevented to be used in combination with a drug other than drugs for the purpose of removing immunosuppression caused by cancer.

A drug for the purpose of removing immunosuppression caused by cancer include, for example, anti-PD-1 antibodies (nivolumab, pembrolizumab, etc.), anti-PD-L1 antibodies (atezolizumab, durvalumab, averumab, etc.), anti-CTLA-4 antibodies (ipilimumab, tremelimumab, etc.), IDO enzyme activity inhibitors (1-methyl-tryptophan, epacadostat, indoximod, etc.), and TDO enzyme activity inhibitors (E)-

6-Fluoro-3-[2-(3-pyridyl)vinyl]-1H-indole (680C91), trans-6-Fluoro-3-[2-(1H-tetrazol-5-yl)vinyl]-1H-indole (LM10), etc.), but are not limited thereto.

Preferably, a composition for inhibiting the growth and/or invasion of a tumor cell of the present invention, and an enhancer of anti-tumor effect of a drug for the purpose of removing immunosuppression caused by cancer of the present invention are used in combination with anti-PD-1 antibody and/or anti-PD-L1 antibody. More preferably, a composition for inhibiting the growth and/or invasion of a tumor cell of the present invention, and an enhancer of anti-tumor effect of a drug for the purpose of removing immunosuppression caused by cancer of the present invention include a Src inhibitor, and are used in combination with anti-PD-1 antibody and/or anti-PD-L1 antibody. Combined use of a Src inhibitor and anti-PD-1 antibody and/or anti-PD-L1 antibody, particularly combined use of a Src inhibitor and anti-PD-1 antibody may provide a better anti-tumor effect.

A composition for inhibiting the growth and/or invasion of a tumor cell of the present invention, and an enhancer of anti-tumor effect of a drug for the purpose of removing immunosuppression caused by cancer of the present invention may contain additives that can be used in medicine, such as a pharmaceutically acceptable carrier, a diluent, excipients and stabilizers. Such additives may be appropriately selected based on common technical knowledge of those skilled in the art.

A composition for inhibiting the growth and/or invasion of a tumor cell of the present invention and an enhancer of anti-tumor effect of a drug for the purpose of removing immunosuppression caused by cancer of the present invention may be particularly useful in a cancer patient who was treated with an IDO enzyme activity inhibitor and for which the IDO enzyme activity inhibitor is no longer effective. This is because the action point of a phosphorylation inhibitor or a dephosphorylation agent against phosphorylation of a tyrosine residue(s) at the 111-th position and/or the 249-th position of human IDO1 or a tyrosine residue(s) of non-human IDO1 at a position(s) corresponding to the 111-th position and/or the 249-th position of human IDO1 is different from that of an IDO enzyme activity inhibitor.

One embodiment of the present invention relates to a method for obtaining data to identify a subject suitable for administration of a composition for inhibiting the growth and/or invasion of a tumor cell or an enhancer of anti-tumor effect of a drug for the purpose of removing immunosuppression caused by cancer, wherein the method includes:

detecting, in a tumor cell obtained from the subject, phosphorylation of:

a tyrosine residue(s) at the 111-th position and/or the 249-th position of human IDO1; or a tyrosine residue(s) of non-human IDO1 at a position(s) corresponding to the 111-th position and/or the 249-th position of human IDO1, and wherein the composition or the enhancer of anti-tumor effect includes a phosphorylation inhibitor or a dephosphorylation agent against phosphorylation of the tyrosine residue(s).

The tyrosine residue(s) of non-human IDO1 at a position(s) corresponding to the 111-th position and/or the 249-th position of human IDO1 is/are as described above. Further, the phosphorylation inhibitor or the dephosphorylation agent against the phosphorylation of the tyrosine residue(s) is also as described above.

The specific step of detecting phosphorylation of a tyrosine residue(s) at the 111-th position and/or the 249-th position of human IDO1 or a tyrosine residue(s) of non-human IDO1 at a position(s) corresponding to the 111-th position and/or the 249-th position of human IDO1 in a tumor cell obtained from a subject includes for example, contacting an antibody that specifically binds to IDO1 phosphorylated on the specific tyrosine residue(s) with a tumor tissue or a tumor cell obtained from a subject or IDO1 produced from the tumor cell, and detecting an antigen-antibody reaction. The contact between an antibody and a tumor tissue or a tumor cell or IDO1 is performed, but is not limited to, for example, by adding the antibody to a tumor tissue section or a medium containing a tumor cell, or a medium containing IDO1 or an extract derived from a tumor cell, and incubating them. The detection of an antigen-antibody reaction may be performed by a method well known to those skilled in the art, and includes, but is not limited to, immunohistochemistry, western blotting, ELISA, EIA, surface plasmon resonance, and the like. An antigen-antibody reaction may also be detected by labeling an antibody and/or an antigen with an enzyme, a fluorescent substance, a luminescent substance, a radioisotope, or the like, and performing a measurement method using the physical and/or chemical properties of the label.

An antibody that specifically binds to IDO1 phosphorylated on the specific tyrosine residue(s) can be prepared by using a well-known antibody preparation technique. For example, in the case of an antibody that specifically binds to IDO1 in which a tyrosine residue at the 249-th position of human IDO1 is phosphorylated, a desired antibody can be obtained by immunizing an animal such as mouse, rabbit, rat, hamster, a guinea pig, chicken, goat, or sheep using a peptide of a sequence around the phosphorylated tyrosine at the 249-th position of human IDO1 as an antigen, and collecting the produced antibody from the blood of the animal, and purifying the antibody. Such an antibody may be a polyclonal antibody or a monoclonal antibody.

The above-mentioned antibody is used as an antibody for identifying a subject suitable for administration of a composition for inhibiting the growth and/or invasion of a tumor cell or an enhancer of anti-tumor effect of a drug for the purpose of removing immunosuppression caused by cancer. Therefore, according to one embodiment of the present invention, an antibody is provided to identify a subject suitable for administration of a composition for inhibiting the growth and/or invasion of a tumor cell or an enhancer of anti-tumor effect of a drug for the purpose of removing immunosuppression caused by cancer, wherein the antibody is for detecting, in a tumor cell obtained from the subject, phosphorylation of:

a tyrosine residue(s) at the 111-th position and/or the 249-th position of human IDO1; or a tyrosine residue(s) of non-human IDO1 at a position(s) corresponding to the 111-th position and/or the 249-th position of human IDO1 and wherein the composition or the enhancer of anti-tumor effect includes a phosphorylation inhibitor or a dephosphorylation agent against the phosphorylation of the tyrosine residue(s).

The tyrosine residue(s) of non-human IDO1 at a position(s) corresponding to the 111-th position and/or the 249-th position of human IDO1 is/are as described above. And, the phosphorylation inhibitor or the dephosphorylation agent against the phosphorylation of the tyrosine residue(s) is also as described above.

One embodiment of the present invention relates to a method for screening a candidate substance for a composition for inhibiting the growth and/or invasion of a tumor cell or for an enhancer of anti-tumor effect of a drug for the purpose of removing immunosuppression caused by cancer, wherein the method includes:

ex vivo measuring inhibition activity or dephosphorylation activity of a test substance against phosphorylation of:
a tyrosine residue(s) at the 111-th position and/or the 249-th position of human IDO1; or
a tyrosine residue(s) of non-human IDO1 at a position(s) corresponding to the 111-th position and/or the 249-th position of human IDO1; and
selecting the candidate substance based on the measured inhibition activity or dephosphorylation activity of the test substance.

The tyrosine residue(s) of non-human IDO1 at a position(s) corresponding to the 111-th position and/or the 249-th position of human IDO1 is/are as described above.

As used herein, "screening" refers to selecting a desired substance having a certain property from test substances (evaluation target substances).

The specific step for ex vivo measuring inhibition activity or dephosphorylation activity of a test substance against phosphorylation of a tyrosine residue(s) at the 111-th position and/or the 249-th position of human IDO1 or a tyrosine residue(s) of non-human IDO1 at a position(s) corresponding to the 111-th position and/or the 249-th position of human IDO1 may include, for example, but is not limited to, the following:

(1) A step of contacting the test substance with IDO1 possible to be phosphorylated on tyrosine residue(s) at the specific position(s), or with a cell producing IDO1 possible to be phosphorylated on tyrosine residue(s) at the specific position(s); and
(2) A step of detecting phosphorylated tyrosine residue(s) at the specific position(s) in IDO1;

The step (1) can be performed using a technique well known to those skilled in the art, for example, it may be performed by adding both the test substance and IDO1 to a vehicle and incubating them, or adding the test substance in a medium containing a cell producing IDO1 or a medium containing IDO1 or an extract containing IDO1 derived from the cell, and incubating them.

The step (2) can be carried out using a technique well-known to those skilled in the art, for example, it may be performed by adding an antibody that specifically binds to IDO1 phosphorylated on the specific tyrosine residue(s) to a vehicle, medium or extract containing IDO1 or a cell that has been contacted with the test substance in the above-mentioned step (1), and incubating them, and by measuring the amount of phosphorylated tyrosine at the specific position(s) in IDO1 through the detection of an antigen-antibody reaction. As an antibody that specifically binds to IDO1 phosphorylated on the specific tyrosine residue(s), the above-described antibody may be used. The amount of phosphorylated tyrosine can be measured by a method well-known to those skilled in the art, and can be performed by a western blot method, an ELISA method, or the like.

The specific step of selecting a candidate substance based on the measured phosphorylation inhibitory activity or dephosphorylation activity of a test substance includes, for example, comparing the amount of phosphorylated tyrosine at the specific position(s) in IDO1 in the absence of the test substance with the amount of phosphorylated tyrosine at the specific position(s) in IDO1 detected in the presence of the test substance. Such a comparison can be performed using a technique well known to those skilled in the art, for example, it may be performed by comparing the amount of phosphorylated tyrosine measured in the above step (2) with the amount of phosphorylated tyrosine measured in the same manner except that the amount is measured in the absence of the test substance. As a result of the comparison, if the amount of phosphorylated tyrosine measured in the presence of the test substance is less than the amount of phosphorylated tyrosine measured in the absence of the test substance, the test substance is evaluated as having tyrosine phosphorylation inhibitory activity or dephosphorylation activity against the phosphorylation of tyrosine residue(s) at the specific position(s) in IDO1 The test substance having such a phosphorylation inhibitory activity or a dephosphorylation activity is the candidate substance for a composition for inhibiting the growth and/or invasion of a tumor cell, or for an enhancer of anti-tumor effect of a drug for the purpose of removing immunosuppression caused by cancer.

One embodiment of the present invention relates to a method for screening a candidate substance to suppress expression of Slug gene induced by phosphorylation of IDO1 or synthesis of Slug induced by phosphorylation of IDO1, wherein the method includes:

ex vivo measuring inhibition activity or dephosphorylation activity of a test substance against phosphorylation of:
a tyrosine residue(s) at the 111-th position and/or the 249-th position of human IDO1; or
a tyrosine residue(s) of non-human IDO1 at a position corresponding to the 111-th position and/or the 249-th position of human IDO1; and
selecting the candidate substance based on the measured inhibition activity or dephosphorylation activity of the test substance.

The tyrosine residue(s) of non-human IDO1 at a position(s) corresponding to the 111-th position and/or the 249-th position of human IDO1 is/are as described above.

Slug is a transcription factor involved in epithelial-mesenchymal transition and is known to be involved in metastasis of tumor cells. For example, the amino acid sequence of human Slug is shown in SEQ ID NO: 3, and the amino acid sequence of mouse Slug is shown in SEQ ID NO: 4.

The present inventors newly found that Slug expressed in a tumor cell suppresses anti-tumor immunity, that activation of AhR in a tumor cell suppresses anti-tumor immunity, that by the suppression of the Slug gene, suppression of anti-tumor immunity by AhR activated in a tumor cell is remarkably removed and the anti-tumor immune activity is enhanced, and that IDO1 expressed in a tumor cell induces the expression of Slug, which can be suppressed by inhibiting IDO1 enzyme activity, but also by inhibiting phosphorylation of the specific tyrosine residue(s).

The specific step of ex vivo measuring inhibition activity or dephosphorylation activity of a test substance against phosphorylation of a tyrosine residue(s) at the 111-th position and/or the 249-th position of human IDO1 or a tyrosine residue(s) of non-human IDO1 at a position corresponding to the 111-th position and/or the 249-th position of human IDO1 is the same as described above in the method for screening a candidate substance for a composition for inhibiting the growth and/or invasion of a tumor cell, or an enhancer of anti-tumor effect of a drug for the purpose of removing immunosuppression caused by cancer.

The specific step of selecting a candidate substance based on the measured phosphorylation inhibitory activity or dephosphorylation activity of a test substance is the same as described above in the method for screening a candidate substance for a composition for inhibiting the growth and/or invasion of a tumor cell, or an enhancer of anti-tumor effect of a drug for the purpose of removing immunosuppression caused by cancer. The test substance that can be evaluated as having a phosphorylation inhibitory activity or a dephosphorylation activity against the phosphorylation of the specific tyrosine residue(s) in IDO1 is a candidate substance to suppress expression of Slug gene induced by phosphorylation of IDO1 or synthesis of Slug induced by phosphorylation of IDO1.

One embodiment of the present invention relates to a method for screening a candidate substance for a composition for inhibiting the growth and/or invasion of a tumor cell or for an enhancer of anti-tumor effect of a drug for the purpose of removing immunosuppression caused by cancer, wherein the method includes:

ex vivo measuring inhibition activity by a test substance against Src or Slug, inhibition activity by a test substance against a factor which activates Src or Slug, synthesis of Src or Slug by a test substance, or expression of Src gene or Slug gene by a test substance; and selecting the candidate substance based on the measured inhibition activity by the test substance against Src or Slug, the measured inhibition activity by the test substance against a factor which activates Src or Slug, measured synthesis inhibition of Src or Slug by the test substance, or measured expression inhibition of Src gene or Slug gene by the test substance, and wherein the composition or the enhancer of anti-tumor effect is used for a tumor cell in which a tyrosine residue(s) at the 111-th position and/or the 249-th position of human IDO1, or a tyrosine residue(s) of non-human IDO1 at a position(s) corresponding to the 111-th position and/or the 249-th position of human IDO1 is/are phosphorylated, or used for a subject who carries the tumor cell.

The tyrosine residue(s) of non-human IDO1 at a position(s) corresponding to the 111-th position and/or the 249-th position of human IDO1 is/are as described above.

The specific step of ex vivo measuring inhibition activity by a test substance against Src or Slug, inhibition activity by a test substance against a factor which activates Src or Slug, synthesis of Src or Slug by a test substance, or expression of Src gene or Slug gene by a test substance may include, for example, but is not limited to, the following:

(1') A step of contacting the test substance with Src, Slug, a cell that produces Src, or a cell that produces Slug; and (2') A step of detecting phosphorylation of a specific tyrosine residue in Src (tyrosine residue at the 530-th position in human Src), detecting nuclear localization of Slug, measuring Src production, measuring Slug production, measuring the Src gene expression level, or measuring the Slug gene expression level.

The step (1') can be performed using a technique well-known to those skilled in the art, for example, it may be performed by adding the test substance and Src or Slug to a vehicle and incubating them, or by adding the test substance to a medium containing a Src-producing cell or a Slug-producing cell, or a medium containing Src or Slug, or an extract containing Src or Slug, derived from the cell, and incubating them.

The step (2') can be performed using a technique well-known to those skilled in the art. In one embodiment, the step (2'), for example, may be performed by adding an antibody that specifically binds to human Src in which tyrosine at position 530 is phosphorylated to a vehicle, medium or extract containing Src or a cell producing Src that has been contacted with the test substance in the above-mentioned step (1'), and incubating them, and by measuring the amount of phosphorylated tyrosine at position 530 in human Src through the detection of an antigen-antibody reaction. As an antibody that specifically binds to human Src in which tyrosine at position 530 is phosphorylated, a commercially available antibody may be used, or an antibody may be produced using antibody production techniques well known to those skilled in the art. The amount of phosphorylated tyrosine can be measured by western blotting, ELISA, or the like.

In one embodiment, as the step (2'), for example, it may be performed by adding an antibody that specifically binds to Src or Slug to a vehicle, medium or extract containing a Src-producing cell or a Slug-producing cell that has been contacted with the test substance in the above-mentioned step (1), and incubating them, and by measuring the amount of Src production or Slug production through the detection of an antigen-antibody reaction. As an antibody that specifically binds to Src or Slug, a commercially available antibody may be used, or an antibody may be produced using an antibody production technique well known to those skilled in the art. The amount of Src production or Slug production can be measured by a method well known to those skilled in the art, and can be performed by western blotting, ELISA, or the like.

In one embodiment, as the step (2'), for example, it may be performed by extracting RNA from a Src-producing cell or a Slug-producing cell that has been contacted with the test substance in the above-mentioned step (1), and by measuring the Src gene expression level or Slug gene expression level by a quantitative PCR method.

The specific step of selecting a candidate substance based on the measured Src or Slug inhibitory activity by a test substance, or the measured inhibitory activity on a factor that activates Src or Slug by a test substance, or the measured Src or Slug synthesis inhibition by a test substance, or the measured Src gene or Slug gene expression inhibition by a test substance includes, for example, comparing the measurement result in the absence of the test substance with the measurement result in the presence of the test substance. Such a comparison can be performed using techniques well known to those skilled in the art, for example, it may be performed by comparing the amount of phosphorylated tyrosine at a specific site in Src (position 530 in human Src), the amount of Src production, the amount of Slug production, the amount of Src gene expression or the amount of Slug gene expression, measured in the above-mentioned step (2'), with those measured in the same manner except that the measurement is performed in the absence of the test substance.

As a result of the comparison, if the amount of phosphorylated tyrosine at a specific site in Src (position 530 in human Src) measured in the presence of the test substance is higher than that measured in the absence of the test substance, the test substance is a candidate substance for a composition for inhibiting the growth and/or invasion of a tumor cell, or for an enhancer of anti-tumor effect of a drug for the purpose of removing immunosuppression caused by cancer. In addition, as a result of the comparison, if the amount of Src production, the amount of Slug production, the amount of Src gene expression or the amount of Slug gene expression measured in the presence of the test substance are smaller than those measured in the absence of the test substance, the test substance is a candidate substance for a composition for inhibiting the growth and/or invasion of a tumor cell, or for an enhancer of anti-tumor effect of a drug for the purpose of removing immunosuppression caused by cancer.

One embodiment of the present invention relates to a method for screening a candidate substance for inhibiting expression of Slug gene or inhibiting synthesis of Slug, wherein the method includes:

ex vivo measuring Slug inhibition activity by a test substance, inhibition activity against a factor which activates Slug by a test substance, expression of Slug gene by a test substance, or synthesis of Slug by a test substance, in a cell in which a tyrosine residue(s) at the 111-th position and/or the 249-th position of human IDO1, or a tyrosine residue(s) of non-human IDO1 at a position(s) corresponding to the 111-th position and/or the 249-th position of human IDO1 is/are phosphorylated, and/or in a cell in which AhR is activated; and selecting the candidate substance based on the measured Slug inhibition activity by the test substance, the inhibition activity against a factor which activates Slug by the test substance, measured expression inhibition of Slug gene by the test substance, or measured synthesis inhibition of Slug by the test substance.

The tyrosine residue(s) of non-human IDO1 at a position(s) corresponding to the 111-th position and/or the 249-th position of human IDO1 is/are as described above.

The specific step of ex vivo measuring Slug inhibition activity by a test substance, inhibition activity against a factor which activates Slug by a test substance, expression of Slug gene by a test substance, or synthesis of Slug by a test substance, in a cell in which a tyrosine residue(s) at the 111-th position and/or the 249-th position of human IDO1, or a tyrosine residue(s) of non-human IDO1 at a position(s) corresponding to the 111-th position and/or the 249-th position of human IDO1 is/are phosphorylated, and/or in a cell in which AhR is activated may include, for example, but is not limited to, the following step:

(1") A step of contacting the test substance with a cell in which a tyrosine residue(s) at the 111-th position and/or the 249-th position of human IDO1 or a tyrosine residue(s) of non-human IDO1 at a position(s) corresponding to the 111-th position and/or the 249-th position of human IDO1 is/are phosphorylated, and/or with a cell in which AhR is activated, and/or with Slug produced from the cell; and (2") A step of detecting nuclear localization of Slug, measuring the amount of Slug production, or measuring the amount of Slug gene expression.

The step (1") can be performed using a technique well-known to those skilled in the art, for example, it may be performed by adding the test substance to a medium containing a cell in which a tyrosine residue(s) at the 111-th position and/or the 249-th position of human IDO1, or a tyrosine residue(s) of non-human IDO1 at a position(s) corresponding to the 111-th position and/or the 249-th position of human IDO1 is/are phosphorylated, and/or a cell in which AhR is activated, and/or to a medium or a vehicle containing Slug produced from the cell, or an extract derived from the cell, containing Slug produced therefrom, and incubating.

The step (2") can be performed using a technique known to those skilled in the art. As the step (2"), in one embodiment, for example, it may be performed by adding an antibody that specifically binds to Slug to a medium, vehicle or extract containing a cell or Slug that has been contacted with the test substance in the above-mentioned step (1"), and incubating them, and by measuring the amount of Slug produced through the detection of an antigen-antibody reaction. As an antibody that specifically binds to Slug, a commercially available antibody may be used, or it may be produced using an antibody production technique well known to those skilled in the art. The measurement of the amount of Slug production can be performed by a method known to those skilled in the art, and can be performed by western blotting, ELISA, or the like.

In one embodiment, as the step (2"), for example, it may be performed by extracting RNA from a cell that have been contacted with the test substance in the step (1"), and by measuring the Slug gene expression level by a quantitative PCR method.

The specific step of selecting the candidate substance based on the measured Slug inhibition activity by the test substance, the inhibition activity against a factor which activates Slug by the test substance, measured expression inhibition of Slug gene by the test substance, or measured synthesis inhibition of Slug by the test substance includes, for example, a step of comparing the measurement result in the absence of the test substance with the measurement result in the presence of the test substance. Such a comparison can be performed using a technique well-known to those skilled in the art, for example, it may be performed by comparing the amount of Slug production or the amount of Slug gene expression measured in the above step (2") with those measured in the same manner except that the measurement is performed in the absence of the test substance.

As a result of the comparison, if the amount of Slug production or the amount of Slug gene expression measured in the presence of the test substance is less than those measured in the absence of the test substance, the test substance is the candidate substance for inhibiting expression of Slug gene or inhibiting synthesis of Slug.

Further, it is preferable to measure the AhR activity in a cell that has contacted with the test substance in the step (1"). It is preferable to, by comparing this measurement result with the measurement result in the absence of the test substance, measure the influence of the test substance on the AhR activity. In this case, if the test substance has no effect on the AhR activity and the amount of Slug production or the amount of Slug gene expression measured in the presence of the test substance is less than those measured in the absence of the test substance, the test substance may be an inhibitor of a signal transduction pathway involved in the induction of the Slug gene expression originated from AhR activation, or may be an inhibitor of Slug to be synthesized by this expression induction. The measurement of AhR activity can be performed by a method known to those skilled in the art, for example, by detecting expression of Cyp1a1.

Further, it is preferable to measure the phosphorylation of the tyrosine residue(s) in the cell that has been contacted with the test substance in the step (1"). It is preferable to, by comparing this measurement result with the measurement result in the absence of the test substance, measure the influence of the test substance on the phosphorylation of the tyrosine residue(s). In this case, if the test substance has no effect on the phosphorylation of the tyrosine residue(s), and the amount of Slug production or the amount of Slug gene expression measured in the presence of the test substance is less than those measured in the absence of the test substance, the test substance may be an inhibitor of a signal transduction pathway involved in the induction of the Slug gene expression originated from the phosphorylation of the tyrosine residue(s), or may be an inhibitor of Slug to be synthesized by this expression induction. The measurement of the phosphorylation of the tyrosine residue(s) can be performed according to the method described above.

Further, in this screening method, it is preferable to use both a cell in which a tyrosine residue(s) at the 111-th position and/or the 249-th position of human IDO1, or a tyrosine residue(s) of non-human IDO1 at a position(s) corresponding to the 111-th position and/or the 249-th position of human IDO1 is/are phosphorylated, and a cell in which AhR is activated. By comparing the obtained measurement results, it may be determined whether the test substance is an inhibitor of a signal transduction pathway involved in the induction of the Slug gene expression originated from AhR activation, or an inhibitor of Slug to be synthesized by the induction of the Slug gene expression originated from AhR activation, or an inhibitor of a signal transduction pathway involved in the induction of the Slug gene expression originated from the phosphorylation of the tyrosine residue(s), or an inhibitor of Slug to be synthesized by the induction of the Slug gene expression originated from the phosphorylation of the tyrosine residue(s).

EXAMPLES

Hereinafter, the present invention will be described in more detail with reference to specific examples, but the scope of the present invention is not limited to these examples.

Example 1

Preparation of Cancer Cells Transfected and Constitutively Expressed with Genes
1. Preparation of Mutant Genes
The introduction of the Y111F, Y249F, and H346A mutations into human IDO1, the introduction of the Y115F, Y253F, and H350A mutations into mouse IDO1 and the introduction of the Y530F mutation into human Src were performed using the Kunkel method.

The constitutively active human AhR gene was prepared by joining the nucleotide sequence corresponding to the region from amino acids 1 to 294 and the region from amino acids 428 to 848 of human AhR after PCR amplification. The constitutively active mouse AhR gene was prepared by joining the nucleotide sequence corresponding to the region from amino acids 1 to 288 and the region from amino acids 422 to 805 of mouse AhR after PCR amplification.
2. Gene Transfer into Cancer Cells
Lentivirus was used for constitutive gene expression in cancer cells (mouse cancer cell MCA205, human cancer cell SW837). Genes were inserted into the multi cloning site (MCS) of the lentivirus vector CSII-CDF-MCS-IRES-puro-PRE, and these were transfected into 293T cells together with the envelope plasmid pCMV-VSV-G-RSV-Rev and the packaging plasmid pMDLg/pRRE. After the transfection, the lentivirus was concentrated from the culture supernatant. Cancer cells were infected with the lentivirus, and puromycin was added for selection, thereby establishing constitutively expressing strains of the genes. For comparison, a cell line infected with a lentivirus prepared from an empty vector without gene insertion was prepared.

Example 2

Evaluation of the Effect of IDO1 or Active Form of AhR Gene Expression on Tumor Growth in Mouse Cancer Cells MCA205

$1\times10^6$ cancer cells were implanted subcutaneously on the ventral side of C57BL/6 mice, and the major axis and minor axis of the tumor were measured every two days. The tumor volume was calculated as $0.5\times$(major axis)$\times$(minor axis)$^2$.

The cancer cells were prepared according to 2. of Example 1 and the following was used.
MCA205 transfected with empty vector without gene insertion (MCA205 mock)
MCA205 in which a wild-type mouse IDO1 gene was transfected and constitutively expressed (MCA205 IDO1)
MCA205 in which a constitutively active mouse AhR gene was transfected and constitutively expressed (MCA205 actAhR)

FIG. 1 shows the average value and the standard deviation of the tumor volume for each group (n=5). Due to the effects of IDO1 gene expression and AhR gene expression, an increase in tumor volume was observed in each case.

Example 3

Evaluation of the Effect of IDO1 Mutations on Tumor Growth in Mouse Cancer Cells MCA205
1. Measurement of Tumor Volume
$1\times10^6$ cancer cells were implanted subcutaneously on the ventral side of C57BL/6 mice, and the major axis and minor axis of the tumor were measured every two days. The tumor volume was calculated as $0.5\times$(major axis)$\times$(minor axis).

The cancer cells were prepared according to 2. of Example 1. The following was used.
MCA205 transfected with empty vector without gene insertion (MCA205 mock)
MCA205 in which a wild-type mouse IDO1 gene was transfected and constitutively expressed (MCA205 IDO1WT)
MCA205 in which a mouse IDO1 mutant gene prepared to synthesize IDO1 having an amino acid mutation of H350A was transfected and constitutively expressed (MCA205 IDO1HA)
MCA205 in which a mouse IDO1 mutant gene prepared to synthesize IDO1 having amino acid mutations of Y115F and Y253F was transfected and constitutively expressed (MCA205 IDO1YYFF)

Figure 2:
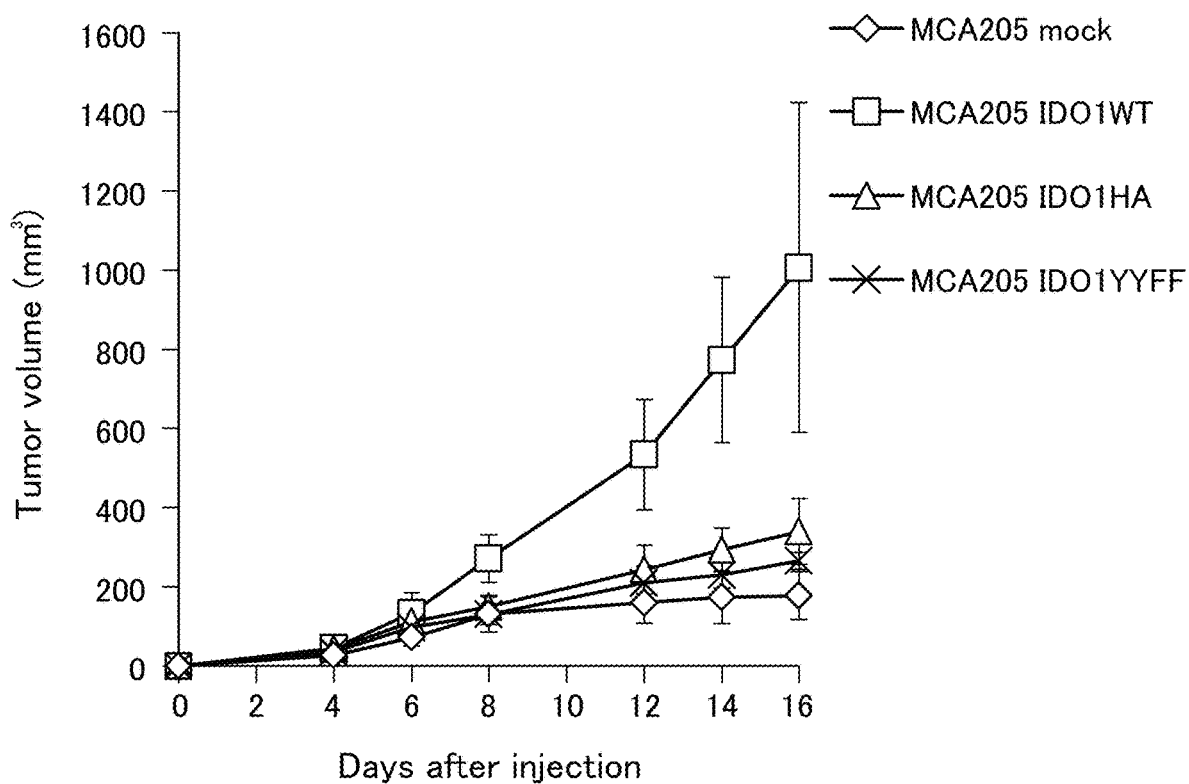
FIG. 2 is a graph showing an increase in tumor volume in C57BL/6 mice implanted with mouse cancer cells MCA205. MCA205 mock represents MCA205 transfected with an empty vector without gene insertion. MCA205 IDO1WT represents MCA205 in which a wild-type mouse IDO1 gene was transfected and constitutively expressed. MCA205 IDO1HA represents MCA205 in which a mouse IDO1 mutant gene prepared to synthesize IDO1 having an amino acid mutation of H350A was transfected and constitutively expressed. MCA205 IDO1YYFF represents MCA205 in which a mouse IDO1 mutant gene prepared to synthesize IDO1 having amino acid mutations of Y115F and Y253F was transfected and constitutively expressed.

FIG. 2 shows the average value and the standard deviation of the tumor volume for each group (n=5). When the wild-type mouse IDO1 gene was expressed, a tumor significantly larger than the mock was formed. On the other hand, when the mouse IDO1 gene mutated to show the amino acid mutation of H350A was expressed, and when the mouse IDO1 gene mutated to show the amino acid mutations of Y115F and Y253F was expressed, small tumors comparable to the mock were formed.

The amino acid mutation H350A in mouse IDO1 reduces the enzyme activity of IDO to metabolizes Trp. Epacadostat and indoximod have been developed as drugs that suppress the enzyme activity of IDO to metabolize Trp, and are used in cancer immunotherapy. In contrast, amino acid mutations of Y115F and Y253F in mouse IDO1 eliminate the phosphorylation sites of ITIMs in IDO1. From the above results, it was shown that tumor growth can be inhibited by eliminating the phosphorylation sites of ITIMs in IDO1, and that its growth inhibitory effect is comparable to inhibiting the enzyme activity of IDO.
2. Evaluation of Antigen-Specific IFN-γ Production
From the mice implanted with the cancer cells as described in 1. above, spleen cells were isolated from the spleens on day 16 after the implantation of the cancer cells. For each group, $2\times10^8$ cells were collectively suspended in 20 ml of a medium RPMI1640 supplemented with 10% FCS and 50 μM 2-mercaptoethanol, and added the H-2$K^b$-restricted epitope peptide KSPWFTTL (SEQ ID NO: 5) of gp70, a cancer antigen, at a concentration of 10 μg/μL and cultured. Five days later, CD8-positive T cells were collected by MACS sorting using CD8a microbeads (Miltenyi Biotec). $1\times10^5$ of collected CD8-positive T cells were cultured with 1×10⁵ of spleen cells from naive mice irradiated with 30 Gy radiation and peptides at a concentration of 0.01, 0.1 or 1.0 µg/mL in a volume of 200 µL using a 96-well plate for 24 hours in 3 wells for each condition. As the peptides, an H-2K$^b$-restricted epitope peptide of gp70, or an H-2K$^b$-restricted epitope peptide of β-galactosidase DAPIYTNV (SEQ ID NO: 6) as a negative control, were used. The culture supernatant after culturing was collected and mouse IFN-γ production, as an indicator of anti-tumor immune activity by cytotoxic T cells, was measured using an OptEIA mouse IFN-γ ELISA set from BD Pharmingen.

Figure 3:
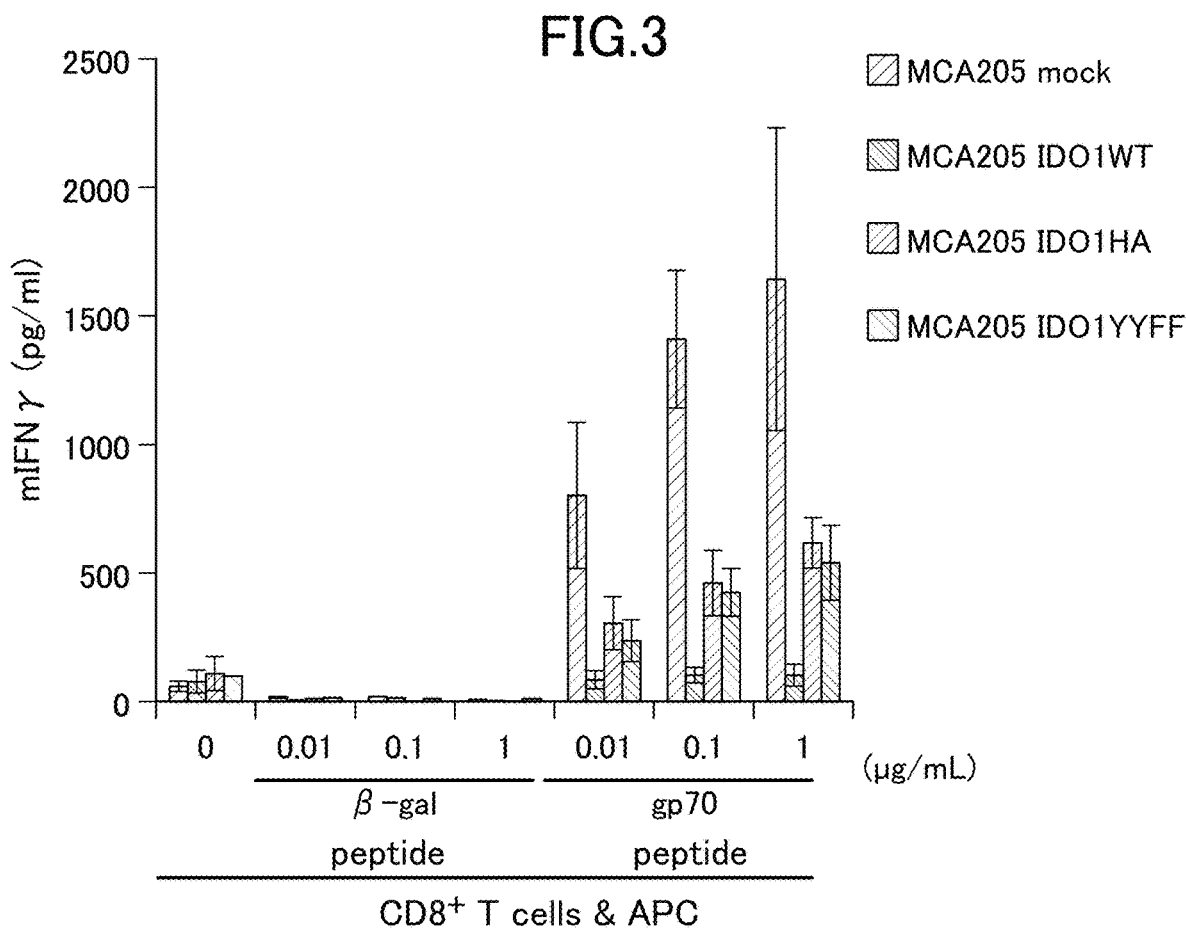
FIG. 3 is a graph showing the amount of mouse IFN-γ, an index of anti-tumor immunity, produced by cytotoxic T cells in C57BL/6 mice implanted with mouse cancer cells MCA205. MCA205 mock, MCA205 IDO1WT, MCA205 IDO1HA and MCA205 IDO1YYFF are the same as those in FIG. 2.

FIG. 3 shows the average and standard deviation of the measured values of the three wells in each condition for each group. When the wild-type mouse IDO1 gene was expressed, IFN-γ production was significantly reduced as compared with the mock, indicating that the anti-tumor immunity was reduced. On the other hand, when the mouse IDO1 gene mutated to show the amino acid mutation of H350A was expressed, and when the mouse IDO1 gene mutated to show the amino acid mutations of Y115F and Y253F was expressed, IFN-γ production is lower than that of the mock, but is higher than when wild-type mouse IDO1 gene is expressed, thus it was shown that the anti-tumor immune activity is enhanced as compared to when wild-type mouse IDO1 gene is expressed.

3. Evaluation of Invasive Ability of Cancer Cells

Using Roche's XCELLigence Syetem and CIM-Plate 16, 20,000 cancer cells suspended in serum-free medium above 2.5% matrigel, medium containing 10% fetal bovine serum below matrigel, and further below an electrode for detecting cells were placed, and the invasive ability of cancer cells was evaluated by detecting the number of cells that reached the electrode as a cell index using electric resistance as an index.

Figure 4:
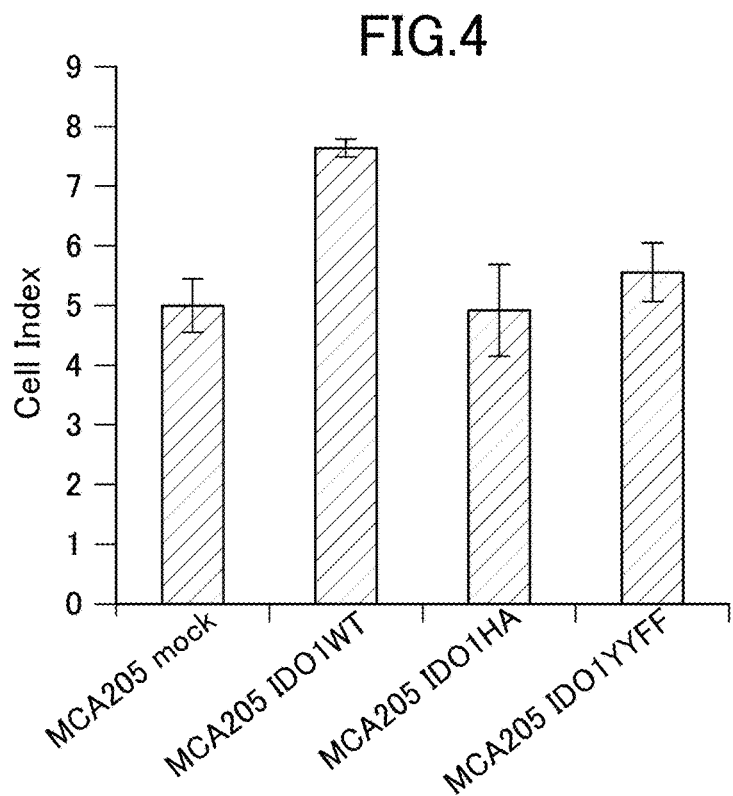
FIG. 4 is a graph which shows the invasion ability of the cancer cells measured by the invasion assay using matrigel. MCA205 mock, MCA205 IDO1WT, MCA205 IDO1HA and MCA205 IDO1YYFF are the same as those in FIG. 2.

The cell index values at 48 hours after the start of the culture are shown in FIG. 4 (n=3). When the wild-type mouse IDO1 gene was expressed, increased invasive ability was observed as compared with the mock. On the other hand, when the mouse IDO1 gene mutated to show the amino acid mutation of H350A was expressed, and when the mouse IDO1 gene mutated to show the amino acid mutations of Y115F and Y253F was expressed, invasive ability equivalent to the mock was observed.

Example 4

Evaluation of the Effects of IDO1 Mutations in Cancer Cells on Slug Gene Expression and Tumor Growth and Anti-Tumor Immunity 1. Immunohistochemical Staining of Cancer Patient Tissue Paraffin sections of colorectal cancer patients and breast cancer patients were stained using VECTOR's VEC-TASTAIN Elite ABC KIT according to the recommended protocol. Antigen retrieval was performed with 10 mM citric acid (pH 6.0). Antibodies prepared as described below were used for staining IDO1 pTyr249, and ab27568 from abcam was used for Slug staining.

<Preparation of Human IDO1 Phosphorylated Tyr249-Specific Antibody>

Rabbits were immunized with a peptide having the sequence of DGLV(pY)EGFWEDPKEFAGGSC (SEQ ID NO: 7) around phosphorylated Tyr249 of human IDO1 as an antigen to prepare an antibody. The antibody to the corresponding non-phosphorylated peptide was absorbed and removed, and the antibody was purified.

Figure 5:
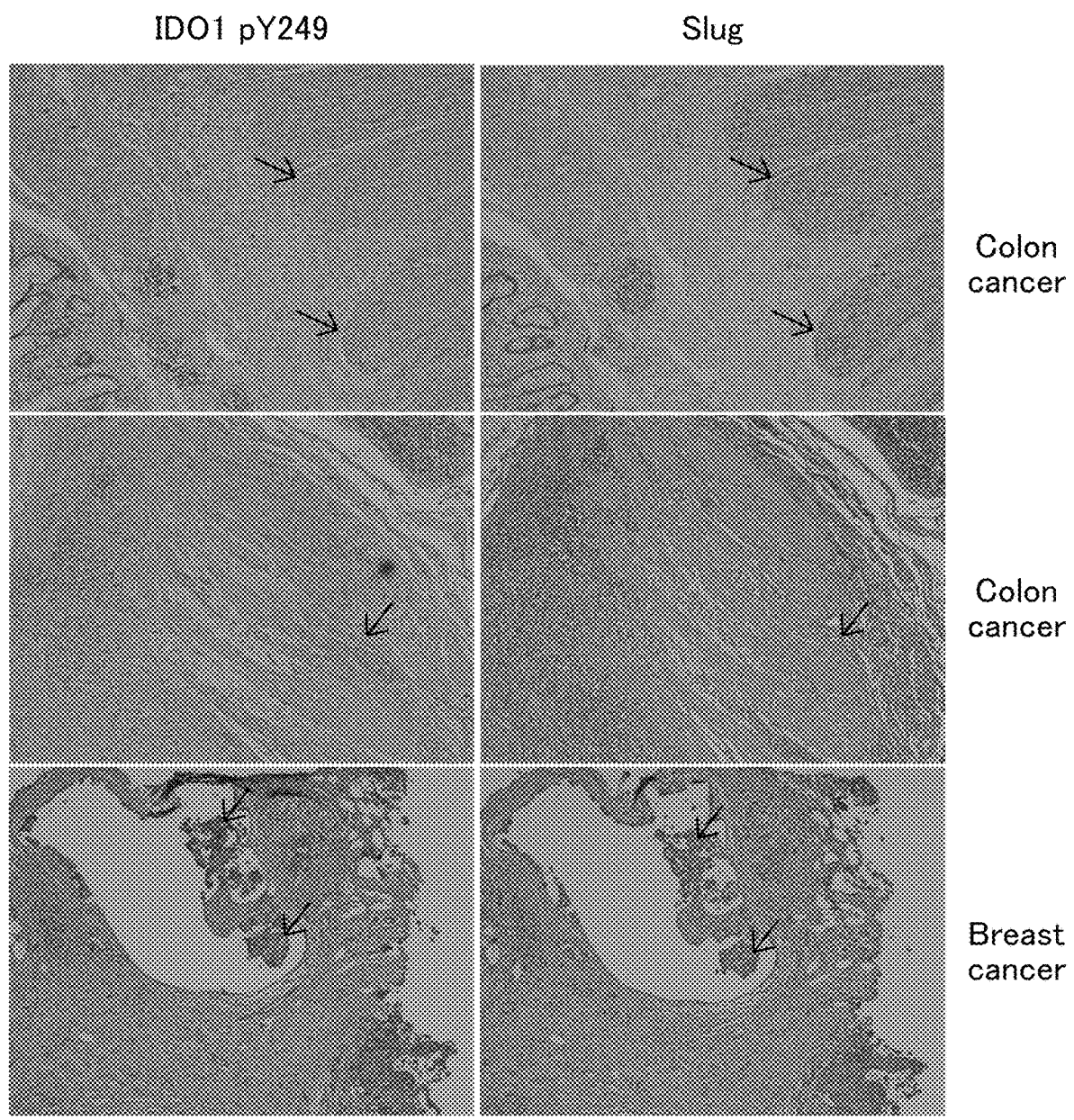
FIG. 5 is photographs showing the phosphorylation of Y249 in IDO1 and the localization of Slug by immunohistochemical staining for tumor tissues derived from colorectal cancer patients and tumor tissues derived from breast cancer patients.

FIG. 5 shows the results of immunohistochemical staining observed with an optical microscope. This showed that the sites where the tyrosine at position 249 (ITIM2) in human IDO1 were phosphorylated coincides with the sites where Slug was highly expressed.

2. Gene Expression Analysis by Quantitative PCR

RNA was extracted from the cancer cells using RNeasy mini kit from QIAGEN, and cDNA was synthesized using oligo dT and Superscript III from Invitrogen. Using 5'-TTACCCAGTGGCCTTTCTCCTC-3' (SEQ ID NO: 8) and 5'-GGTTCGAATGTGCATCTTCAGG-3' (SEQ ID NO: 9) as primers, the amount of mouse Slug gene expression was measured by a quantitative PCR method using CYBER GREEN. And using 5'-GGTTGGCCACTTTGACCCTTAC-3' (SEQ ID NO: 10) and 5'-AACCTCCCCAAACTCAT-TGCTC-3' (SEQ ID NO: 11) as primers, the amount of mouse Cyp1a1 gene expression was measured by a quantitative PCR method using CYBER GREEN. As endogenous controls required for relative comparison, using 5'-CATGACAACTTTGGCATTGTGG-3' (SEQ ID NO: 12) and 5'-GTCCACCACCCTGTTGCTGTAG-3' (SEQ ID NO: 13) as primers, the level of mouse GAPDH expression was measured by a quantitative PCR method using CYBER GREEN.

The cancer cells were prepared according to 2. of Example 1, and the following was used.

MCA205 transfected with empty vector without gene insertion (MCA205 mock)

MCA205 in which a wild-type mouse IDO1 gene was transfected and constitutively expressed (MCA205 IDO1WT)

MCA205 in which a mouse IDO1 mutant gene prepared to synthesize IDO1 having an amino acid mutation of H350A was transfected and constitutively expressed (MCA205 IDO1HA)

MCA205 in which a mouse IDO1 mutant gene prepared to synthesize IDO1 having amino acid mutations of Y115F and Y253F was transfected and constitutively expressed (MCA205 IDO1YYFF)

MCA205 in which a constitutively active mouse AhR gene was transfected and constitutively expressed (MCA205 actAhR)

MCA205 in which a mouse IDO1 mutant gene prepared to synthesize IDO1 having an amino acid mutation of Y115F was transfected and constitutively expressed (MCA205 IDO1Y115F)

MCA205 in which a mouse IDO1 mutant gene prepared to synthesize IDO1 having an amino acid mutation of Y253F was transfected and constitutively expressed (MCA205 IDO1Y253F)

Figure 6:
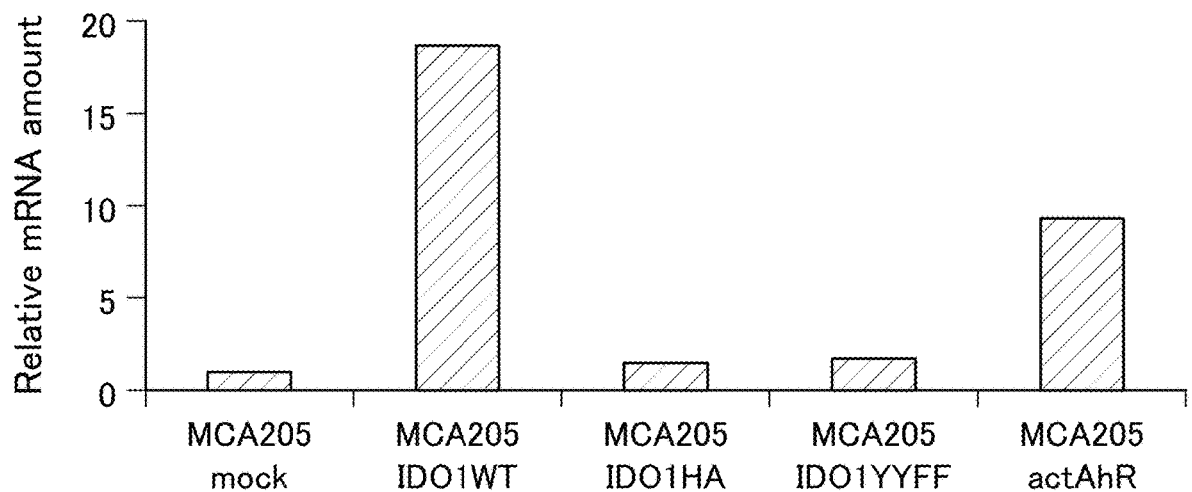
FIG. 6 is a graph showing the results of quantitative PCR analysis of Slug gene expression levels in mouse cancer cells MCA205. MCA205 mock, MCA205 IDO1WT, MCA205 IDO1HA and MCA205 IDO1YYFF are the same as those in FIG. 2. MCA205 actAhR is the same as in FIG. 1. The vertical axis indicates relative values of the amount of mRNA where the amount of mRNA detected in the case of MCA205 mock is set as 1.
Figure 7:
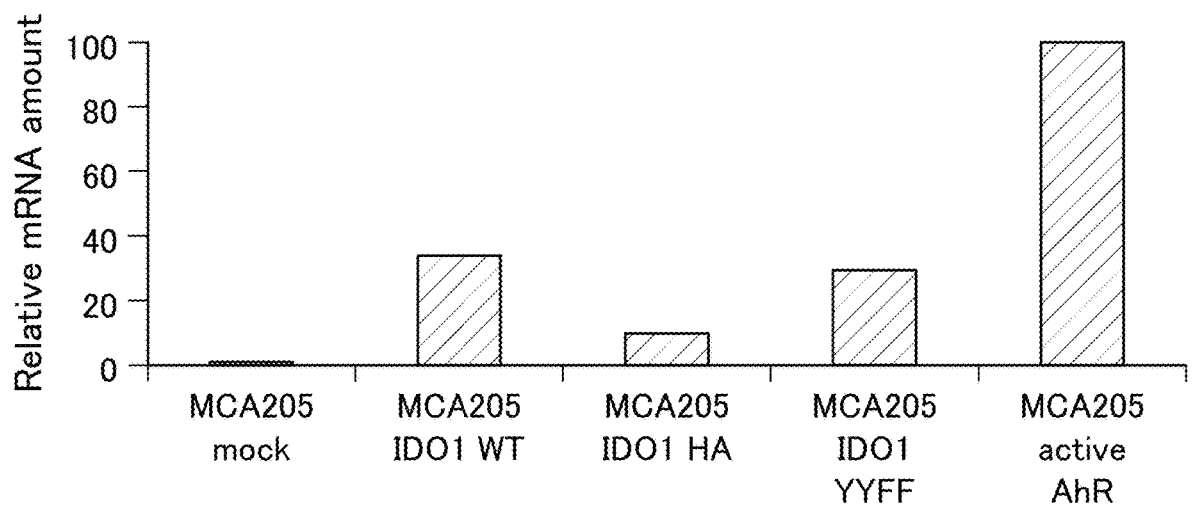
FIG. 7 is a graph showing the results of quantitative PCR analysis of cyp1a1 gene expression levels in mouse cancer cells MCA205. MCA205 mock, MCA205 IDO1WT, MCA205 IDO1HA and MCA205 IDO1YYFF are the same as those in FIG. 2. MCA205 active AhR represents MCA205 in which the constitutively active mouse AhR gene was transfected and constitutively expressed (same as MCA205 actAhR). The vertical axis indicates relative values of the amount of mRNA where the amount of mRNA detected in the case of MCA205 mock is set as 1.

The results are shown in FIG. 6 and FIG. 7. When the wild-type mouse IDO1 gene was expressed, the amount of the mouse Slug gene expression was significantly increased as compared with the mock. Also, when the constitutively active AhR gene was expressed, the amount of the mouse Slug gene expression was significantly increased as compared with the mock. On the other hand, when the mouse IDO1 gene mutated to show the amino acid mutation of H350A was expressed, and when the mouse IDO1 gene mutated to show the amino acid mutations of Y115F and Y253F was expressed, the level of mouse Slug gene expression was significantly lower than that of wild-type mouse IDO1 gene.

Cyp1a1 (cytochrome P450 1A1) is one of the downstream molecules induced by AhR expression, and Cyp1a1 expression is an indicator of AhR activity. When the AhR gene was expressed, the expression level of the mouse Cyp1a1 gene was significantly increased (the value of MCA205 active AhR is 219.97). In addition, when the wild-type mouse IDO1 gene was expressed, and when the mouse IDO1 gene mutated to show amino acid mutations of Y115F and Y253F was expressed, the level of mouse Cyp1a1 gene expression was increased as compared with the mock.

Figure 8:
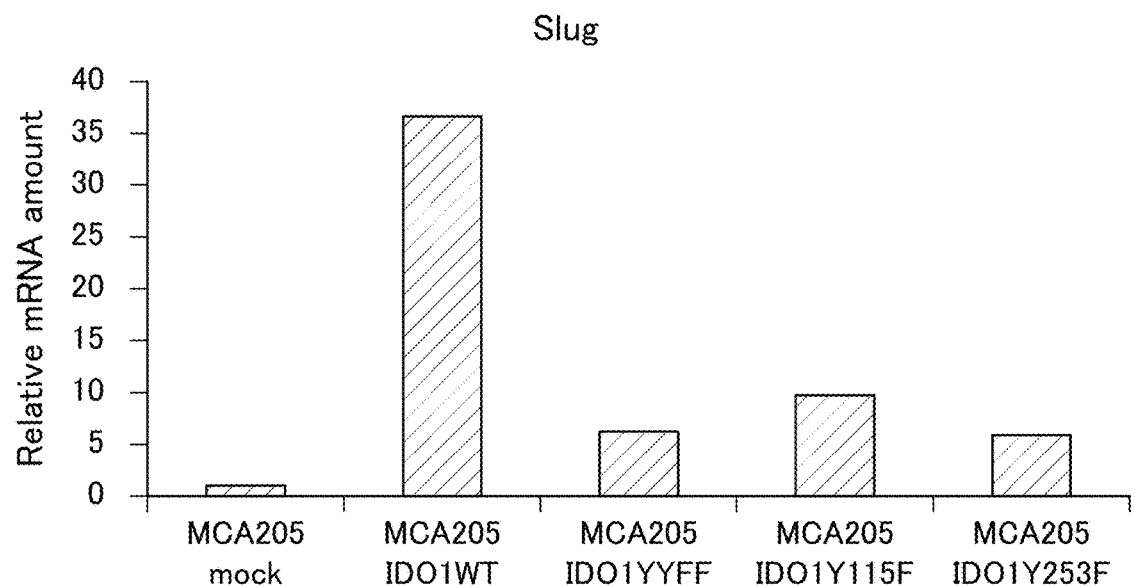
FIG. 8 is a graph showing the results of quantitative PCR analysis of Slug gene expression levels in mouse cancer cells MCA205. The MCA205 mock, MCA205 IDO1WT and MCA205 IDO1YYFF are the same as those in FIG. 2. MCA205 IDO1Y115F represents MCA205 in which a mouse IDO1 mutant gene prepared to synthesize IDO1 having an amino acid mutation of Y115F was transfected and constitutively expressed. MCA205 IDO1Y253F represents MCA205 in which a mouse IDO1 mutant gene prepared to synthesize IDO1 having an amino acid mutation of Y253F was transfected and constitutively expressed. The vertical axis indicates relative values of the amount of mRNA where the amount of mRNA detected in the case of MCA205 mock is set as 1.

FIG. 8 shows the effect of the single mutation of Y115F or Y253F of mouse IDO1 on mouse Slug gene expression. When the wild-type mouse IDO1 gene was expressed, the level of the mouse Slug gene expression was significantly increased as compared with the mock, and when the mouse IDO1 gene mutated to show the amino acid mutations of Y115F and Y253F in is expressed, the level of the mouse Slug gene expression was significantly lower than that of wild-type mouse IDO1 gene. When the mouse IDO1 gene mutated to show the amino acid mutation of Y115F was expressed, and when the mouse IDO1 gene mutated to show the amino acid mutation of Y253F was expressed, the level of the mouse Slug gene expression was significantly lower than that of wild-type mouse IDO1 gene.

From the above results, it has been shown that loss of the phosphorylation sites of ITIMs in IDO1 does not seem to show much difference from wild-type IDO1 from the viewpoint of the effect on AhR activity, but it significantly suppresses the expression of Slug gene.

3. Measurement of Tumor Volume $1 \times 10^6$ cancer cells were implanted subcutaneously on the ventral side of C57BL/6 mice, and the major axis and minor axis of the tumor were measured every two days. The tumor volume was calculated as 0.5×(major axis)×(minor axis).

The following were used as cancer cells.

MCA205 transfected with empty vector without gene insertion (MCA205 mock)

MCA205 in which a mouse Slug gene was transfected and constitutively expressed (MCA205 Slug)

Figure 9:
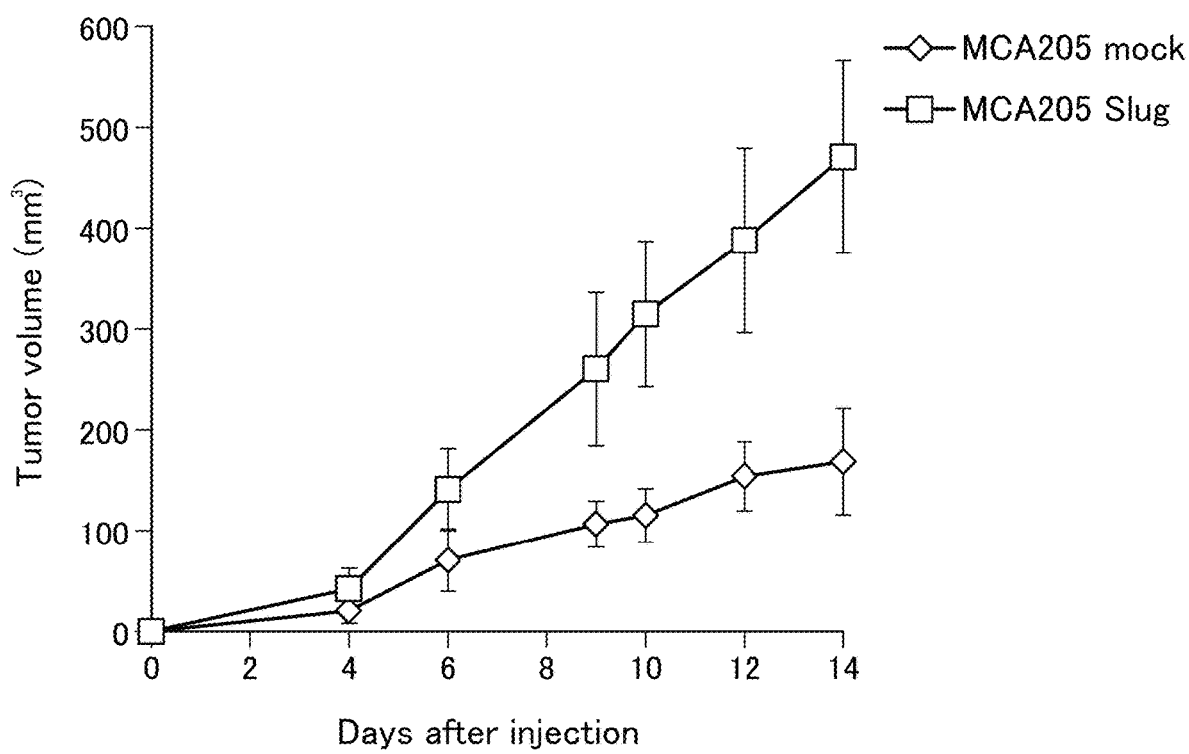
FIG. 9 is a graph showing an increase in tumor volume in C57BL/6 mice implanted with mouse cancer cells MCA205. MCA205 mock represents MCA205 transfected with an empty vector without gene insertion. MCA205 Slug represents MCA205 in which Slug gene was transfected and constitutively expressed.

FIG. 9 shows the average value and the standard deviation of the tumor volume for each group (n=5). When the mouse Slug gene was expressed, a tumor significantly larger than the mock was formed. This indicated that the Slug gene promoted tumor growth.

4. Evaluation of Antigen-Specific IFN-γ Production

The amount of mouse IFN-γ production was measured in the same manner as in 2. of Example 3, except that spleen cells were isolated from the spleens 14 days after the implantation of the cancer cells from the mice implanted with the cancer cells as described in the 3 above, and CD8-positive T cells were collected by MACS sorting using CD8a microbeads 6 days after the start of the culture.

Figure 10:
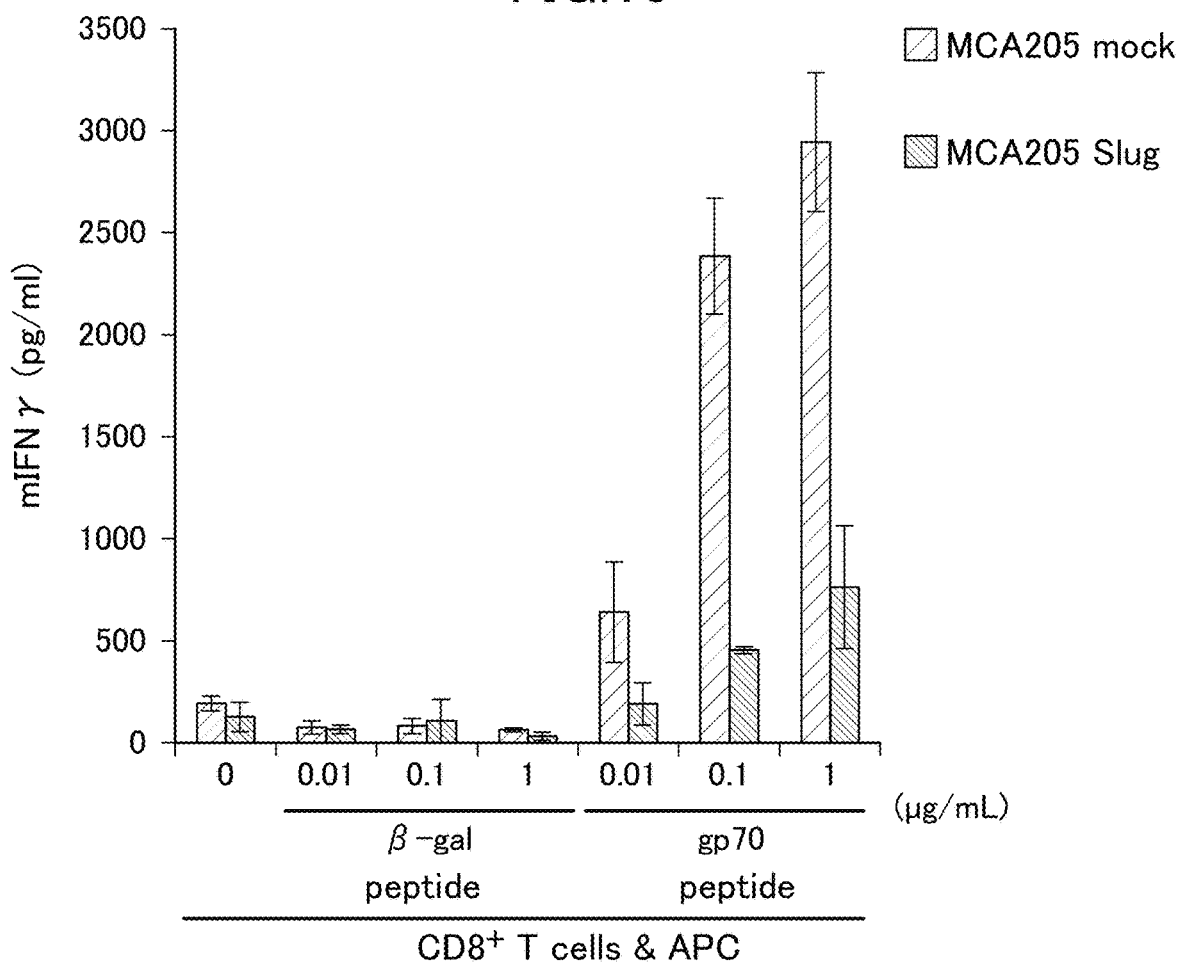
FIG. 10 is a graph showing the amount of mouse IFN-γ, an index of anti-tumor immunity, produced by cytotoxic T cells in C57BL/6 mice implanted with mouse cancer cells MCA205. MCA205 mock and MCA205 Slug are the same as those in FIG. 9.

FIG. 10 shows the average and standard deviation of the measured values of the three wells under each condition for each group. When the mouse Slug gene was expressed, the production of IFN-γ was significantly reduced compared with that of the mock, indicating that the anti-tumor immunity was reduced.

Example 5

Evaluation of the Effect of Slug Induced by AhR Activation on Tumor Growth and Anti-Tumor Immunity 1. Knockdown of Slug Gene Expression by shRNA For knockdown of Slug gene expression by shRNA, a lentivirus vector HIV-U6i-blast was used. For knockdown of mouse Slug, shRNA having GCAGACCCACTCT-GATGTAAA (SEQ ID NO: 14) as a target sequence was used. As a negative control, NonTarget shRNA having a non-specific sequence CAACAAGATGAAGAGCACCAA (SEQ ID NO: 15) as a target sequence was used. The lentiviral vector made by inserting the target sequence was transfected into 293T cells together with the envelope plasmid pCMV-VSV-G-RSV-Rev and the packaging plasmid pMDLg/pRRE, and the lentivirus was concentrated from the culture supernatant. The lentivirus thus prepared was infected to MCA205 in which a constitutively active mouse AhR gene was transfected and constitutively expressed obtained by gene transfection as described in 2. of Example 1, and after infection blasticidin S hydrochloride was added for selection, a stable knockdown cell line was established and designated as MCA205 actAhR shSlug. The one into which NonTarget shRNA was introduced was designated as MCA205 actAhR NonTarget.

2. Gene Expression Analysis by Quantitative PCR

RNA was extracted from the cells prepared as described above (MCA205 actAhR shSlug and MCA205 actAhR NonTarget) using a RNeasy mini kit from QIAGEN, and cDNA was synthesized using oligo dT and Superscript III from Invitrogen. Using 5'-TTACCCAGTGGCCTTTCTCCTC-3' and 5'-GGTTCGAATGTGCATCTTCAGG-3' as primers, the amount of mouse Slug gene expression was measured by a quantitative PCR method using CYBER GREEN. As an endogenous control required for the relative comparison, the expression level of mouse GAPDH was measured by a quantitative PCR method using CYBER GREEN using 5'-CATGACAACTTTGGCATTGTGG-3' and 5'-GTCCAC-CACCCTGTTGCTGTAG-3' as primers.

Figure 11:
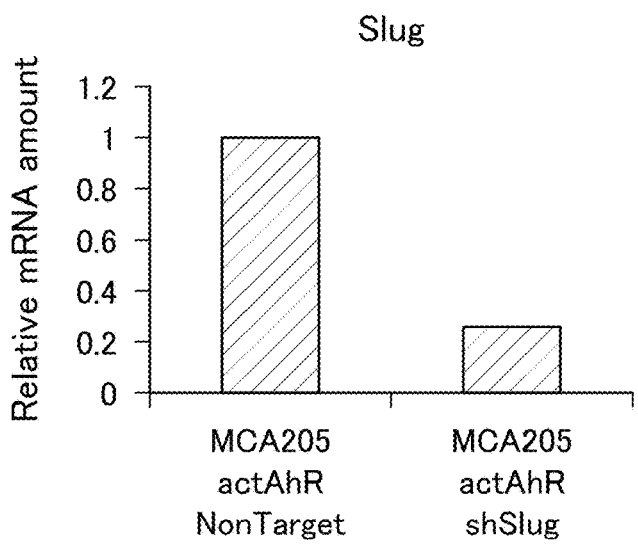
FIG. 11 is a graph showing the results of quantitative PCR analysis of Slug gene expression levels in mouse cancer cells MCA205. MCA205 actAhR shSlug represents MCA205 in which a constitutively active mouse AhR gene was introduced and constitutively expressed, and Slug gene expression is constitutively knocked down. MCA205 actAhR NonTarget represents a negative control. The vertical axis indicates relative values of the amount of mRNA where the amount of mRNA detected in the case of MCA205 actAhR NonTarget is set as 1.

The results are shown in FIG. 11. Compared with MCA205 actAhR NonTarget, MCA205 actAhR shSlug in which Slug gene expression was stably knocked down significantly reduced the amount of mouse Slug gene expression.

3. Measurement of Tumor Volume $1 \times 10^6$ cancer cells were implanted subcutaneously on the ventral side of C57BL/6 mice, and the major axis and minor axis of the tumor were measured every two days. The tumor volume was calculated as 0.5×(major axis)×(minor axis).

The following were used as cancer cells.

MCA205 transfected with empty vector without gene insertion (MCA205 mock)

MCA205 in which the constitutively active mouse AhR gene was transfected and constitutively expressed, and the Slug gene expression was stably knocked down (MCA205 actAhR shSlug)

MCA205 in which the constitutively active mouse AhR gene was introduced and constitutively expressed, and NonTarget shRNA has been transfected (MCA205 actAhR NonTarget)

Figure 12:
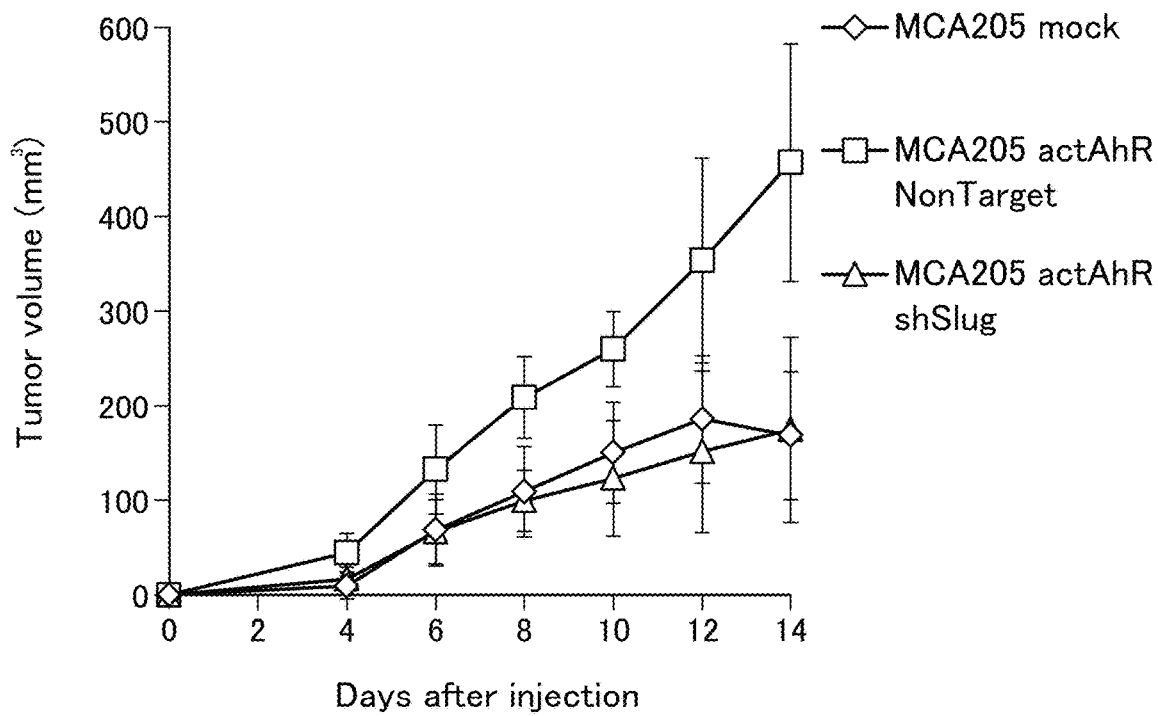
FIG. 12 is a graph showing an increase in tumor volume in mice implanted with mouse cancer cells MCA205. MCA205 mock represents MCA205 transfected with an empty vector without gene insertion. MCA205 actAhR shSlug and MCA205 actAhR NonTarget are the same as those in FIG. 11.

FIG. 12 shows the average value and the standard deviation of the tumor volume for each group (n=5). MCA205 actAhR NonTarget formed a tumor that was significantly larger than the mock. On the other hand, MCA205 actAhR shSlug, in which Slug gene expression was stably knocked down, formed small tumors equivalent to the mock. This indicates that tumor growth can be inhibited by suppressing the Slug gene.

4. Evaluation of Antigen-Specific IFN-γ Production

The amount of mouse IFN-γ production was measured in the same manner as in 2. of Example 3, except that spleen cells were isolated from the spleens 14 days after the implantation of the cancer cells from the mice implanted with the cancer cells as described in the 3 above.

Figure 13:
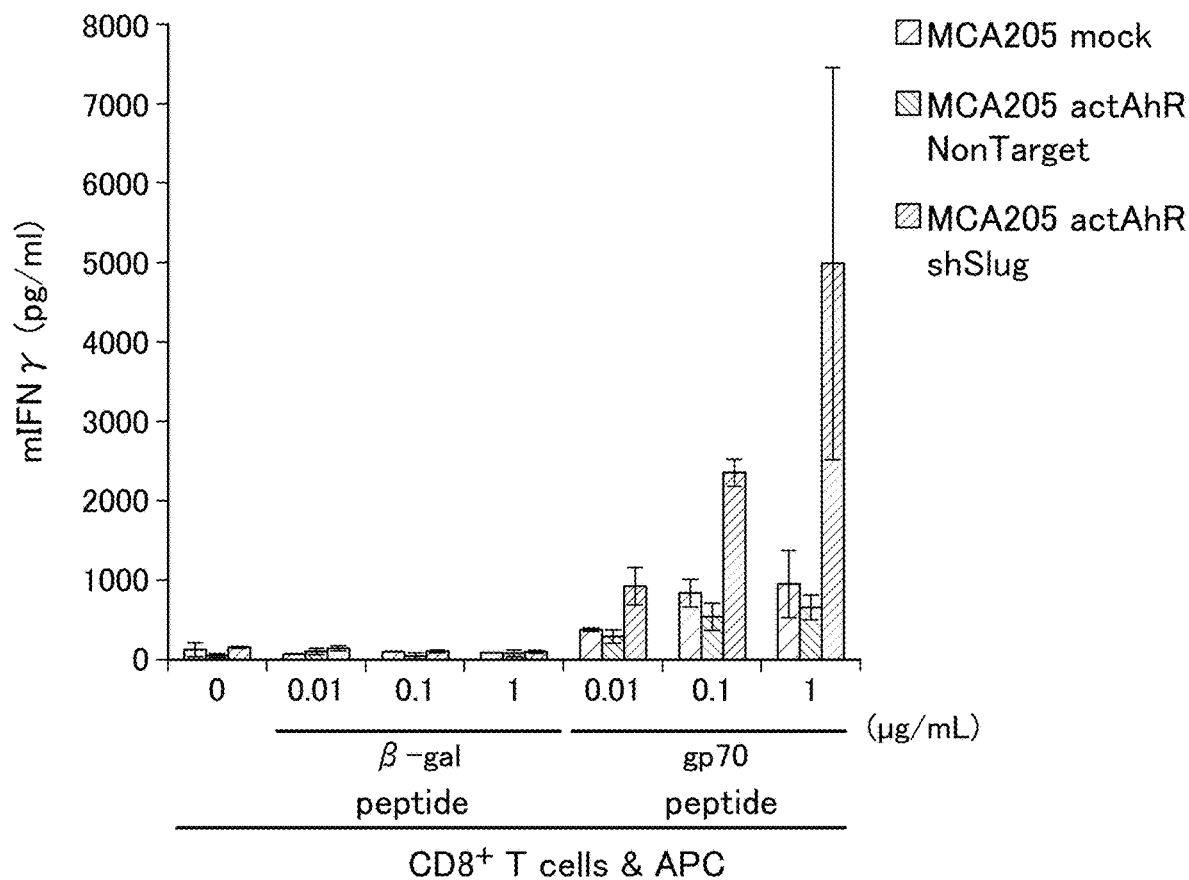
FIG. 13 is a graph showing the amount of mouse IFN-γ, an index of anti-tumor immunity, produced by cytotoxic T cells in C57BL/6 mice implanted with mouse cancer cells MCA205. MCA205 mock, MCA205 actAhR shSlug and MCA205 actAhR NonTarget are the same as those in FIG. 11.

FIG. 13 shows the average and standard deviation of the measured values of the three wells in each condition for each group. In the case of MCA205 actAhR shSlug in which Slug gene expression was stably knocked down, IFN-γ production was significantly increased, indicating that anti-tumor immunity was enhanced.

Example 6

Evaluation of the Effect of IDO1 Mutations on Slug Gene Expression in Human Cancer Cell SW837

RNA was extracted from the cancer cells using RNeasy mini kit from QIAGEN, and cDNA was synthesized using oligo dT and Superscript III from Invitrogen. Using 5'-ACTGTGTGGACTACCGCTGCTC-3' (SEQ ID NO: 16) and 5'-CCCCCGTGTGAGTTCTAATGTG-3' (SEQ ID NO: 17) as primers, the amount of the human Slug gene expression was measured by a quantitative PCR method using CYBER GREEN. As an endogenous control required for the relative comparison, the expression level of human GAPDH was measured by a quantitative PCR method using CYBER GREEN using 5'-TGAACGGGAAGCTCACTGG-3' (SEQ ID NO: 18) and 5'-TCCACCACCCTGTTGCTGTA-3' (SEQ ID NO: 19) as primers.

The cancer cells were prepared according to 2. of Example 1, and the following was used.

SW837 transfected with empty vector without gene insertion (SW837 mock)

SW837 in which a wild-type human IDO1 gene was transfected and constitutively expressed (SW837 IDO1WT)

SW837 in which a human IDO1 mutant gene prepared to synthesize IDO1 having an amino acid mutation of H346A was transfected and constitutively expressed (SW837 IDO1HA)

SW837 in which a human IDO1 mutant gene prepared to synthesize IDO1 having amino acid mutations of Y111F and Y249F was transfected and constitutively expressed (SW837 IDO1YYFF)

SW837 in which a constitutively active human AhR gene was transfected and constitutively expressed (SW837 actAhR)

Figure 14:
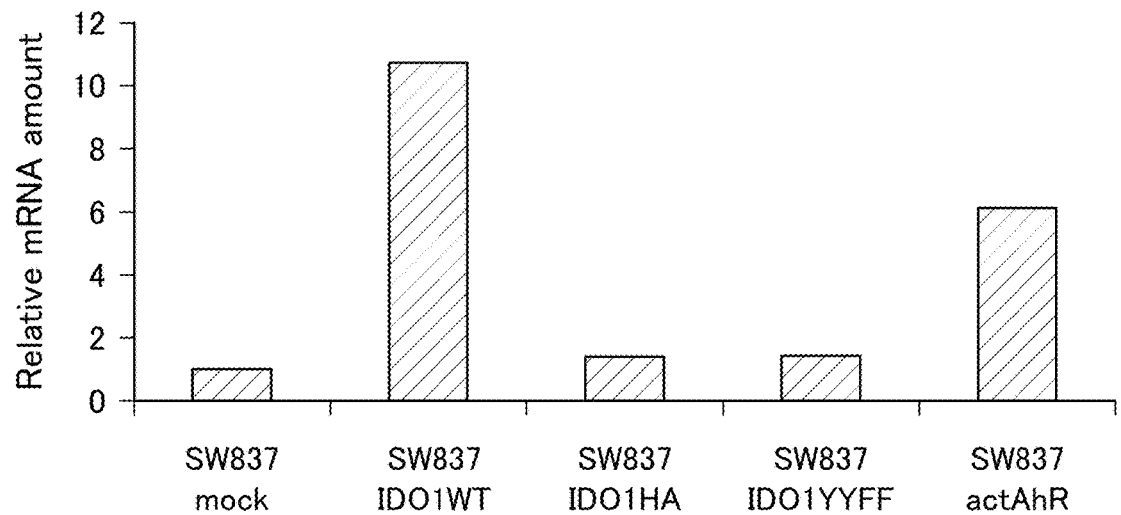
FIG. 14 is a graph showing the results of quantitative PCR analysis of Slug gene expression levels in human cancer cells SW837. SW837 mock represents SW837 transfected with an empty vector without gene insertion. SW837 IDO1WT represents SW837 in which a wild-type human IDO1 gene was transfected and constitutively expressed. SW837 IDO1HA represents SW837 in which a human IDO1 mutant gene prepared to synthesize IDO1 having an amino acid mutation of H346A was transfected and constitutively expressed. SW837 IDO1YYFF represents SW837 in which a human IDO1 mutant gene prepared to synthesize IDO1 having amino acid mutations of Y111F and Y249F was transfected and constitutively expressed. SW837 actAhR represents SW837 in which a constitutively active human AhR gene was introduced and constitutively expressed. The vertical axis indicates relative values of the amount of mRNA where the amount of mRNA detected in the case of SW837 mock is set as 1.

FIG. 14 shows the results. When the wild-type human IDO1 gene was expressed, the amount of the human Slug gene expression was significantly increased as compared with the mock. Similarly, when the constitutively active AhR gene was expressed, the amount of the human Slug gene expression was significantly increased as compared with the mock. On the other hand, when the human IDO1 gene mutated to show the amino acid mutation of H346A was expressed, and when the human IDO1 gene mutated to show the amino acid mutations of Y111F and Y249F was expressed, the level of the human Slug gene expression was equivalent to the mock.

Example 7

Evaluation of the Relationship Between ITIM Phosphorylation and Src in Cancer Cells 1. Immunohistochemical Staining of Cancer Patient Tissues Paraffin sections from colorectal cancer patients were stained using VECTOR's VECTASTAIN Elite ABC KIT according to the recommended protocol. Antigen retrieval was performed with 10 mM citric acid (pH 6.0). For the staining of IDO1 pTyr249, the antibody prepared as described in 1. of Example 4 was used, AF3389 from R&D was used for Src staining, sc-286 from Santa Cruz was used for Csk staining, and Ab60028 antibody from abcam was used for Src pY530 staining.

Csk is a protein that phosphorylates the C-terminal tyrosine of Src and negatively regulates the activity of Src. Src pY530 represents Src in which tyrosine at position 530 is phosphorylated, and the activity of Src is negatively regulated by this phosphorylation.

Figure 15:
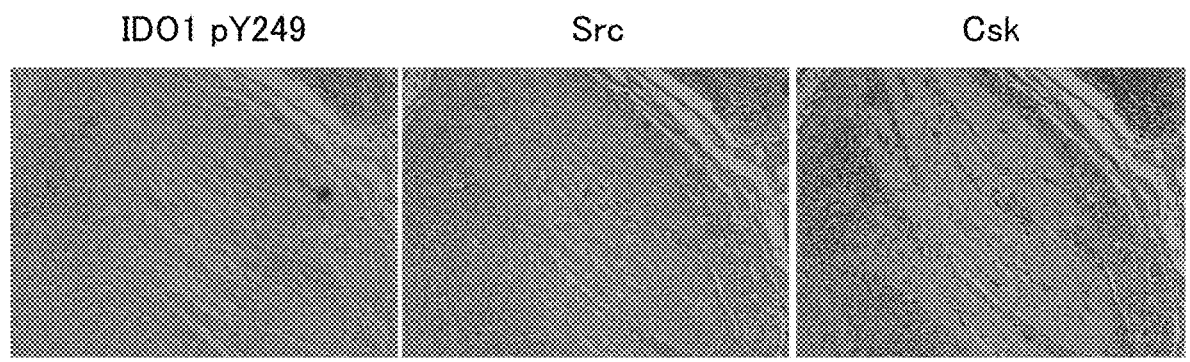
FIG. 15 is photographs showing, by immunohistological staining, sites where Y249 is phosphorylated in IDO1, Src localization, and Csk localization in tumor tissues derived from colorectal cancer patients.
Figure 16:
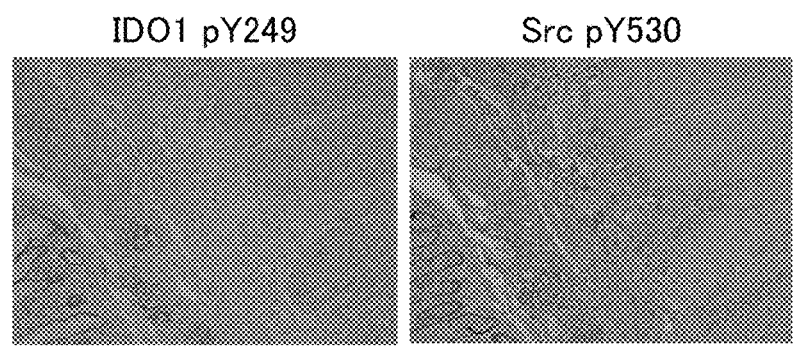
FIG. 16 is a photograph showing, by immunohistological staining, sites where Y249 is phosphorylated in IDO1 and sites where Y530 is phosphorylated in Src in a tumor tissue derived from a colorectal cancer patient.

The results of immunohistological staining observed with an optical microscope are shown in FIG. 15 and FIG. 16. As a result, the sites where the tyrosine at position 249 (ITIM2) in human IDO1 were phosphorylated were in good agreement with the sites where Src was expressed and Csk was not expressed.

2. Identification of a Kinase that Phosphorylates Human IDO1 Tyr249 Expressed in Cancer Cells Human Src Y530F inserted into pcDNA3.1 was transiently transfected with Lipofectamine LTX into human cancer cells SW837 in which a wild-type human IDO1 gene was transfected and constitutively expressed (SW837 IDO1WT), prepared as described in 2. of Example 1. Two days later, the cells were lysed with a cell lysis buffer (20 mM Tris pH 7.4, 150 mM NaCl, 1% NP-40, 0.1% SDS, 0.1% deoxycholate, 1 mM EDTA) supplemented with Roche's phosphatase inhibitor cocktail (PhosSTOP EASYpack) and Roche's protease inhibitor cocktail (complete, EDTA-free), and the cell lysate was electrophoresed on a 10% acrylamide gel and transferred to a PVDF membrane. The phosphorylation of human IDO1 Tyr249 was detected by western blotting using the human IDO1 phosphorylated Tyr249-specific antibody prepared as described in 1. of Example 4, and the entire human IDO1 protein was detected by western blotting using an anti-human IDO1 antibody (Thermo PA1-40279).

Figure 17:
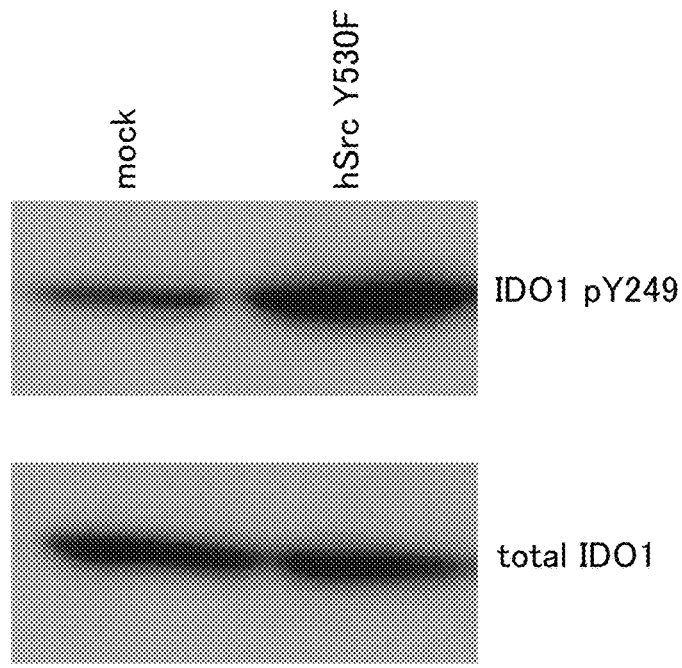
FIG. 17 is a photograph showing protein detection of IDO1 phosphorylated at Y249 and total IDO1 in human cancer cells SW837 in which a wild-type human IDO1 gene was transfected and constitutively expressed. Mock represents a human cancer cell SW837 in which a wild-type human IDO1 gene was transfected and constitutively expressed and an empty vector (pcDNA3.1) without gene insertion was transiently transfected. hSrc Y530F represents SW837 in which a wild-type human IDO1 gene was transfected and constitutively expressed and further a human Src mutant gene prepared to synthesize an activated Src having an amino acid mutation of Y530F was transfected and transiently expressed.

The results are shown in FIG. 17. Expression of human Src Y530F in SW837 IDO1WT cells was shown to enhance tyrosine phosphorylation of human IDO1 Tyr249 (ITIM2). Because in human Src Y530F, phosphorylation of tyrosine at position 530, which negatively regulates the activity of Src, is inhibited, and the expression of the active form human Src Y530F enhances the phosphorylation of tyrosine of ITIM2, Src was shown to be the kinase responsible for tyrosine phosphorylation of ITIM2.

Example 8

Evaluation of the Effect of Amino Acid Mutations on Human IDO1 Protein Level

Wild-type or mutants of IDO1 were inserted into an expression vector pME-FLAG that adds a FLAG tag to the N-terminal side, and the genes were transiently transfected into human cancer cells SW837 using Lipofectamine LTX using this vector. The transfected genes are as follows.

Empty vector without gene insertion (mock)
Wild-type human IDO1 gene (hIDO1 WT)
Human IDO1 mutant gene prepared to synthesize IDO1 having Y111F amino acid mutation (hIDO1 Y111F)
Human IDO1 mutant gene prepared to synthesize IDO1 having Y249F amino acid mutation (hIDO1 Y249F)
Human IDO1 mutant gene prepared to synthesize IDO1 having amino acid mutations of Y111F and Y249F (hIDO1 Y111,249FF)

Figure 18:
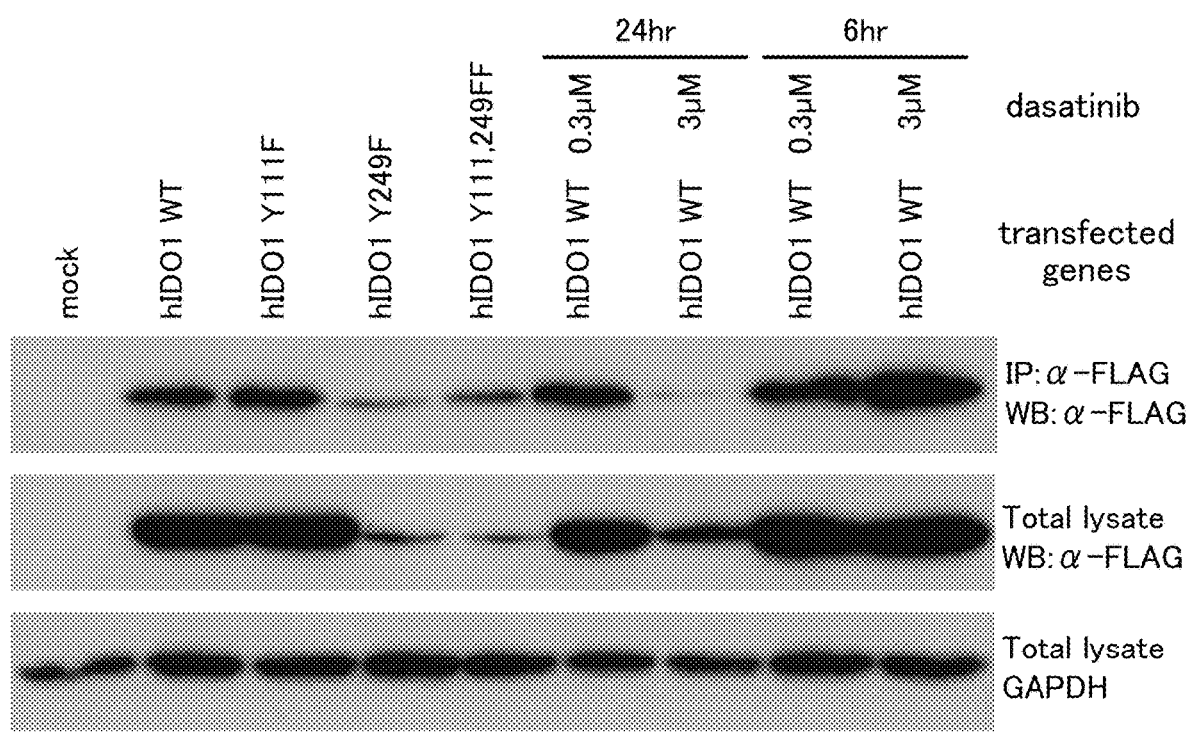
FIG. 18 is a photograph showing the results of detecting a FLAG-fused human IDO1 protein or a GAPDH protein by western blotting in the precipitate after immunoprecipitation with anti-FLAG antibody M2 or in cell extract (Total lysate) before immunoprecipitation from human cancer cells SW837 in which FLAG-tagged human IDO1 was transiently expressed. Mock means use of empty vector without gene insertion (pME-FLAG). hIDO1 WT represents wild type human IDO1 gene. hIDO1 Y111F represents a human IDO1 mutant gene prepared to synthesize IDO1 having an amino acid mutation of Y111F. hIDO1 Y249F represents a human IDO1 mutant gene prepared to synthesize IDO1 having an amino acid mutation of Y249F. hIDO1 Y111,249FF represents a human IDO1 mutant gene prepared to synthesize IDO1 having amino acid mutations of Y111F and Y249F.

Forty hours after gene transfection, the cells were lysed with a cell lysis buffer (20 mM Tris pH7.4, 150 mM NaCl, 1% NP-40, 0.1% SDS, 0.1% deoxycholate, 1 mM EDTA) supplemented with Roche's phosphatase inhibitor cocktail (PhosSTOP EASYpack) and Roche's protease inhibitor cocktail (complete, EDTA-free), and immunoprecipitated with anti-FLAG antibody M2. Dasatinib, a Src inhibitor, was added at a concentration of 0.3 μM or 3 μM 16 hours or 34 hours after transfection of wild-type IDO1. The cell lysate (total lysate) before immunoprecipitation and the immunoprecipitate were each electrophoresed on a 10% acrylamide gel and transferred to a PVDF membrane. IDO1 protein in the immunoprecipitate or total lysate was detected by western blotting using anti-FLAG antibody M2, and GAPDH protein in total lysate was detected by western blotting using anti-GAPDH antibody (Santa Cruz). The results are shown in FIG. 18. When a human IDO1 mutant gene (hIDO1 Y249F) prepared to synthesize IDO1 having an amino acid mutation of Y249F was transfected, and when a human IDO1 mutant gene prepared to synthesize IDO1 having amino acid mutations of Y111F and Y249F was transfected, the amount of IDO1 protein was significantly reduced. It was also shown that the addition of dasatinib, a Src inhibitor, significantly reduced the amount of IDO1 protein in a concentration-dependent and time-dependent manner.

Example 9

Evaluation of the Effect of IDO1 Mutations on Tumor Growth in Mouse Cancer Cell MCA205
1. Measurement of Tumor Volume $1 \times 10^6$ cancer cells were implanted subcutaneously on the ventral side of C57BL/6 mice, and the major axis and minor axis of the tumor were measured every two days. The tumor volume was calculated as $0.5 \times (\text{major axis}) \times (\text{minor axis})^2$.

The cancer cells were prepared according to 2. of Example 1. The following was used.
  MCA205 transfected with empty vector without gene insertion (MCA205 mock)
  MCA205 in which a wild-type mouse IDO1 gene was transfected and constitutively expressed (MCA205 IDO1WT)
  MCA205 in which a mouse IDO1 mutant gene prepared to synthesize IDO1 having an amino acid mutation of Y253F was transfected and constitutively expressed (MCA205 IDO1Y253F)

Figure 19:
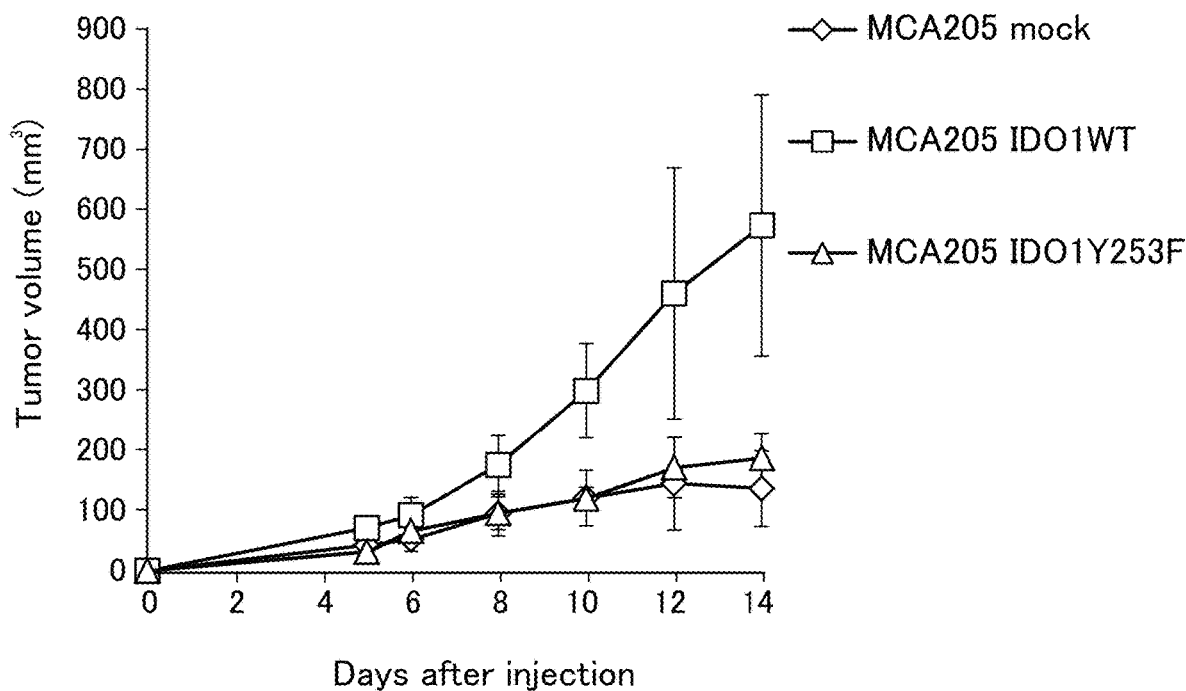
FIG. 19 is a graph showing an increase in tumor volume in C57BL/6 mice implanted with mouse cancer cells MCA205. MCA205 mock represents MCA205 transfected with an empty vector without gene insertion. MCA205 IDO1WT represents MCA205 in which a wild-type mouse IDO1 gene was transfected and constitutively expressed. MCA205 IDO1Y253F represents MCA205 in which a mouse IDO1 mutant gene prepared to synthesize IDO1 having an amino acid mutation of Y253F was transfected and constitutively expressed.

FIG. 19 shows the average value and the standard deviation of the tumor volume for each group (n=5). When the wild-type mouse IDO1 gene was expressed, a tumor significantly larger than the mock was formed. On the other hand, when the mouse IDO1 gene mutated to show the amino acid mutation of Y253F was expressed, a small tumor close to the mock was formed.

The amino acid mutation of Y253F in mouse IDO1 eliminates the phosphorylation site of Y253 in IDO1. The above results indicate that inhibiting the phosphorylation of Y253 alone in IDO1 also has the effect of inhibiting the promotion of tumor growth by IDO1.

Example 10

Combination Therapy of Anti-PD-1 Antibody and Dasatinib in Mice Implanted with MC38 Mouse Cancer Cells
1. Measurement of Tumor Volume On Day 0, $5 \times 10^5$ MC38 were implanted on the ventral side of C57BL/6 mice. MC38 is a mouse cancer cell that expresses IDO1 endogenously.

At 4, 6, and 8 days after implantation (Day 4, Day 6, Day 8), anti-PD-1 antibody (BioXCell, clone RMP-1-14) or the corresponding Rat IgG2a isotype control antibody (BioXCell, clone 2A3) was administered intraperitoneally at 200 µg/animal.

Dasatinib was dissolved in DMSO at 100 mM, diluted with 0.5% methylcellulose, and orally administered at 0.2 mg/100 µl/animal once daily from Day 4. In the control group, a vehicle obtained by diluting DMSO at the same ratio was orally administered at 100 µl/animal once daily from Day 4.

The major axis and minor axis of the tumor were measured every two days. The tumor volume was calculated as $0.5 \times (\text{major axis}) \times (\text{minor axis})^2$.

Figure 20:
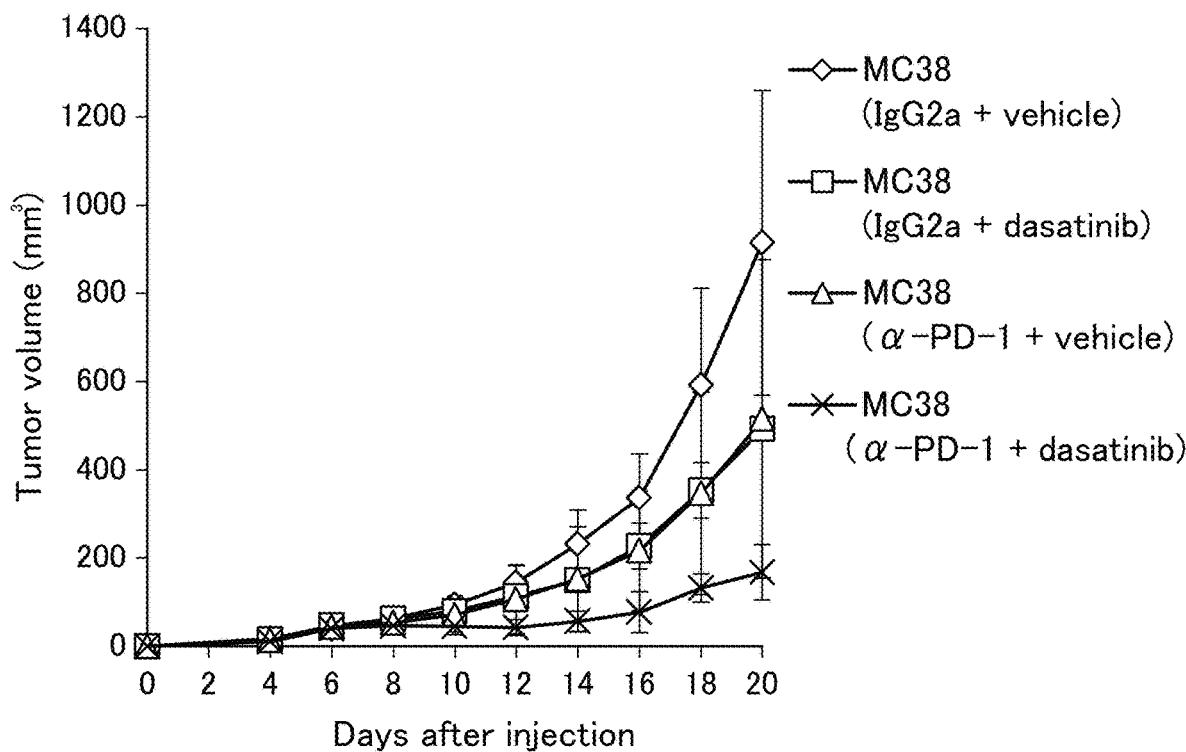
FIG. 20 is a graph showing an increase in tumor volume in C57BL/6 mice implanted with mouse cancer cells MC38. MC38 (IgG2a+vehicle) represents the case where a rat IgG2a isotype control antibody and a vehicle were administered. MC38 (IgG2a+dasatinib) represents the case where a rat IgG2a isotype control antibody and dasatinib were administered. MC38 (α-PD-1+vehicle) represents the case where an anti-PD-1 antibody and a vehicle were administered. MC38 (α-PD-1+dasatinib) represents the case where an anti-PD-1 antibody and dasatinib were administered.

FIG. 20 shows the average value and the standard deviation of the tumor volume for each group (n=5). In the group that received dasatinib alone as a drug and the group that received anti-PD-1 antibody alone as a drug, a smaller tumor was formed as compared to the group that did not receive any of the drugs, and almost equivalent tumor growth inhibitory effect was shown. In the group in which dasatinib and anti-PD-1 antibody were used in combination, remarkable tumor reduction was observed, thus the combination of dasatinib and anti-PD-1 antibody showed an excellent tumor growth inhibitory effect.

2. Evaluation of Antigen-Specific IFN-γ Production

The amount of mouse IFN-γ production was measured in the same manner as in 2. of Example 3, except that spleen cells were isolated from the spleen 20 days after the implantation of the cancer cells from mice implanted with the cancer cells as described in 1 above.

Figure 21:
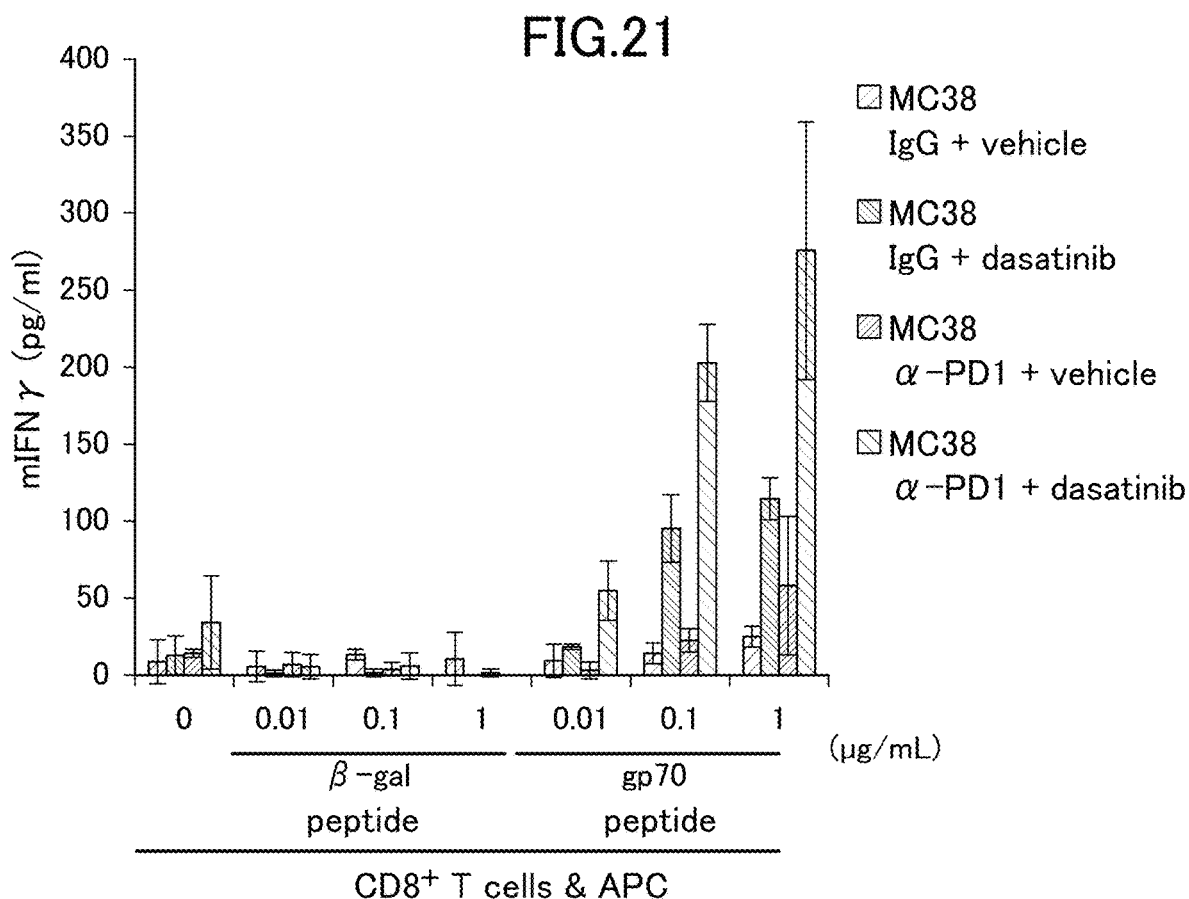
FIG. 21 is a graph showing the amount of mouse IFN-γ, an index of anti-tumor immunity, produced by cytotoxic T cells in C57BL/6 mice implanted with mouse cancer cells MC38. MC38 IgG+vehicle, MC38 IgG+dasatinib, MC38 α-PD1+vehicle, and MC38 α-PD1+dasatinib are the same as MC38 (IgG2a+vehicle), MC38 (IgG2a+ dasatinib), MC38 (α-PD-1+vehicle), and MC38 (α-PD-1+dasatinib) in FIG. 20, respectively.

FIG. 21 shows the average and standard deviation of the measured values of the three wells in each condition for each group. In the group to which dasatinib was administered alone as a drug, the production of IFN-γ was increased and the anti-tumor immunity was enhanced as compared to the group to which no drug was administered. In addition, in the group in which dasatinib was used in combination with anti-PD-1 antibody, the production of IFN-γ was significantly increased, and the anti-tumor immune activity was significantly enhanced.

Example 11

Combination Therapy of Anti-PD-1 Antibody and Dasatinib for Mice Implanted with MCA205 IDO1WT Mouse Cancer Cells Expressing Wild-Type Mouse IDO1 Gene The major axis and minor axis of the tumor, and the tumor volume were measured in the same manner as in 1. of Example 10, except that $5 \times 10^5$ mouse cancer cells MCA205 IDO1WT expressing the wild-type mouse IDO1 gene were implanted to the ventral side of C57BL/6 mice on Day 0.

Figure 22:
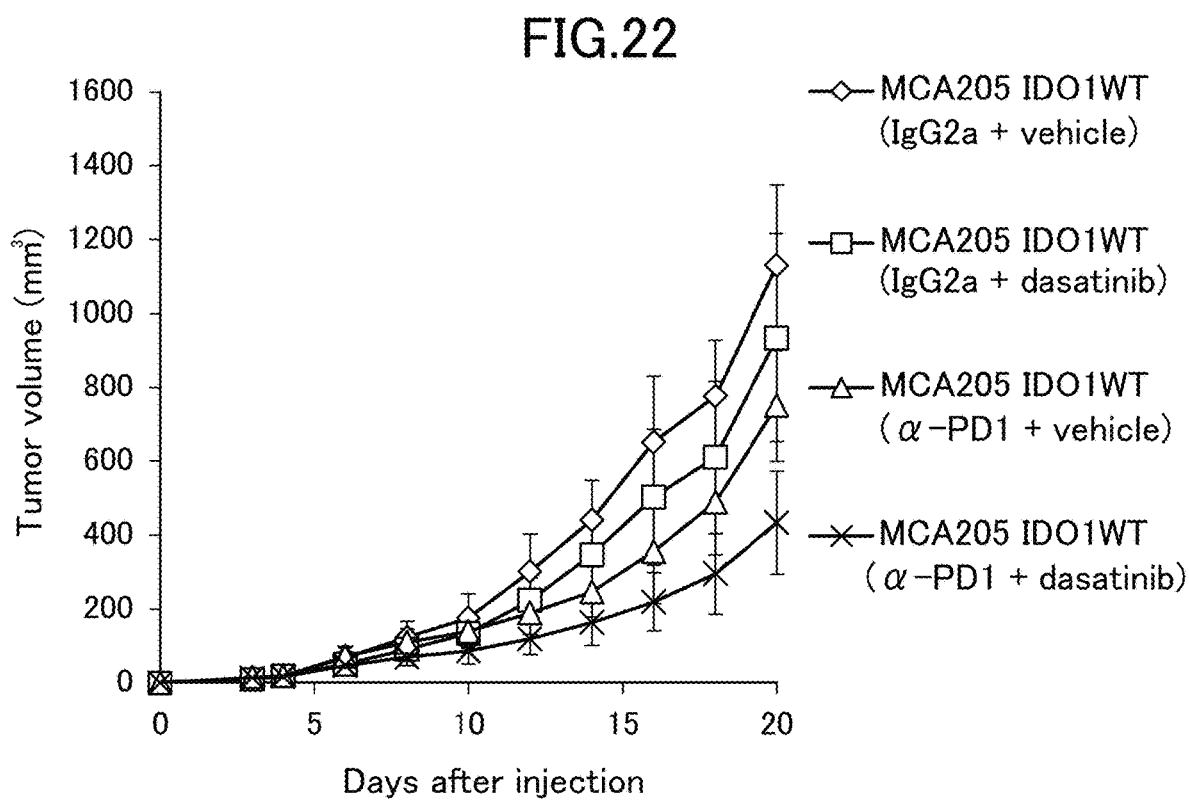
FIG. 22 is a graph showing an increase in tumor volume in C57BL/6 mice implanted with mouse cancer cells MCA205 transfected with a wild-type mouse IDO1 gene. MCA205 IDO1WT (IgG2a+vehicle) represents the case where a rat IgG2a isotype control antibody and a vehicle were administered. MCA205 IDO1WT (IgG2a+ dasatinib) represents the case where a rat IgG2a isotype control antibody and dasatinib were administered. MCA205 IDO1WT (α-PD1+vehicle) represents the case where an anti-PD-1 antibody and a vehicle were administered. MCA205 IDO1WT (α-PD1+ dasatinib) represents the case where an anti-PD-1 antibody and dasatinib were administered.

FIG. 22 shows the average value and the standard deviation of the tumor volume for each group (n=5). In the group to which dasatinib was administered alone as a drug and the group to which anti-PD-1 antibody was administered alone as a drug, a smaller tumor was formed as compared with the group to which neither drug was administered. In the group in which dasatinib and anti-PD-1 antibody were used in combination, remarkable tumor reduction was observed, and the combination of dasatinib and anti-PD-1 antibody showed a remarkable tumor growth inhibitory effect.

Example 12

Combination Therapy of IDO1 Enzyme Activity Inhibitor 1-MT and FAK Inhibitor Y15 on Mice Implanted with MCA205 IDO1WT Mouse Cancer Cells Expressing Wild-Type Mouse IDO1 Gene On Day 0, $5 \times 10^5$ mouse cancer cells MCA205 IDO1WT expressing the wild-type mouse IDO1 gene were implanted into the ventral side of C57BL/6 mice.

From five days after implantation (Day 5), 1-Methyl-D-tryptophan (1-MT, SIGMA, 4 mg/mL aqueous solution adjusted to pH 7.4 with hydrochloric acid after dissolving with 1N NaOH) or water was administered freely from a water bottle.

The FAK inhibitor Y15 (MedChem Express) was dissolved in PBS and administered intraperitoneally once a day from Day 5 at 600 μg/100 μl/animal. In the control group, PBS was intraperitoneally administered at 100 μl/animal once a day from Day 5.

The major axis and minor axis of the tumor were measured every two days. The tumor volume was calculated as $0.5 \times (\text{major axis}) \times (\text{minor axis})^2$.

Figure 23:
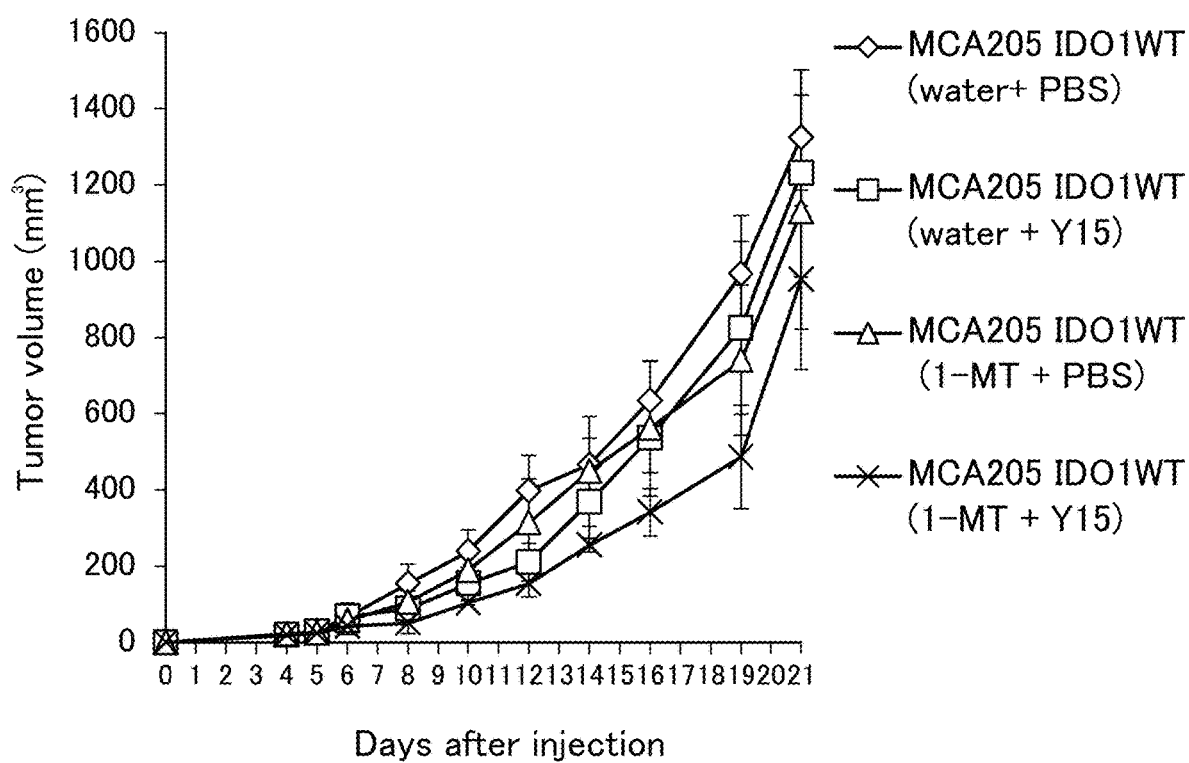
FIG. 23 is a graph showing an increase in tumor volume in C57BL/6 mice implanted with mouse cancer cells MCA205 transfected with a wild-type mouse IDO1 gene. MCA205 IDO1WT (water+PBS) represents the case where water and PBS were administered. MCA205 IDO1WT (water+Y15) represents the case where water and FAK inhibitor Y15 were administered. MCA205 IDO1WT (1-MT+PBS) represents the case where 1-Methyl-D-tryptophan and PBS were administered. MCA205 IDO1WT (1-MT+Y15) represents the case where 1-Methyl-D-tryptophan and the FAK inhibitor Y15 were administered.

FIG. 23 shows the average value and the standard deviation of the tumor volume for each group (n=5). In the group to which Y15 was administered alone as a drug and the group to which 1-MT was administered alone as a drug, a smaller tumor was formed as compared with the group to which neither drug was administered. In the group in which Y15 and 1-MT were used in combination, remarkable tumor reduction was observed, thus the combination of Y15 and 1-MT showed a remarkable tumor growth inhibitory effect.

INDUSTRIAL APPLICABILITY

This invention can be utilized as a cancer therapeutic agent, and can be utilized for the development of a cancer therapeutic agent.

Furthermore, the present invention is expected to be used in cancer immunotherapy, and in particular, it may be useful in combination therapy with a drug for the purpose of removing immunosuppression caused by cancer such as anti-PD-1 antibody, anti-PD-L1 antibody, anti-CTLA-4 antibody and IDO enzyme activity inhibitor.

What is claimed is:

1. A method for inhibiting the growth and/or invasion of a solid tumor, wherein the method includes administering a phosphorylation inhibitor or a dephosphorylation agent against phosphorylation of:
- a tyrosine residue(s) at the 111-th position and/or the 249-th position of human IDO1; or
- a tyrosine residue(s) of non-human IDO1 at a position(s) corresponding to the 111-th position and/or the 249-th position of human IDO1 to a solid tumor comprising a tumor cell in which said human IDO1 or non-human IDO1 tyrosine residue(s) is/are phosphorylated or a subject who carries a solid tumor comprising the tumor cell,
- wherein the phosphorylation inhibitor or the dephosphorylation agent is a Src inhibitor selected from a group consisting of dasatinib, bosutinib, saracatinib, ponatinib, ilorasertib, N-benzyl-2-(5-(4-(2-morpholinoethoxy)phenyl)pyridin-2-yl)acetamide, 4-amino-5-(4-chlorophenyl)-7-(tert-butyl)pyrazolo-[3,4-d]pyrimidine, 4-amino-5-(4-methylphenyl)-7-(tert-butyl)pyrazolo-[3,4-d]pyrimidine, 4-(4'-phenoxyanilino)-6,7-dimethoxyquinazoline, 2-((3,5-di-tert-Butyl-4-hydroxyphenyl)-methylene)-4-cyclopentene-1,3-dione, 4-N-(5-cyclopropyl-1H-pyrazol-3-yl)-6-(4-methylpiperazin-1-yl)-2-N-[(3-propan-2-yl-1,2-oxazol-5-yl)methyl]pyrimidine-2,4-diamine, [7-(2,6-dichloro-phenyl)-5-methyl-benzo[1,2,4]triazin-3-yl]-[4-(2-pyrrolidin-1-yl-ethoxy)-phenyl]-amine, [7-(2,6-dichloro-phenyl)-5-methyl-benzo[1,2,4]triazin-3-yl]-{4-[2-(1-oxy-pyrrolidin-1-yl)-ethoxy]-phenyl}-amine, and rebastinib, and salts, hydrates, and solvates thereof, and
- wherein the method includes further administering a drug to the tumor cell or the subject for the purpose of removing immunosuppression caused by cancer.

2. The method according to claim 1, wherein the drug includes anti-PD-1 antibody or anti-PD-L1 antibody.

3. A method for enhancing anti-tumor effect of a therapy for the purpose of removing immunosuppression caused by cancer, wherein the method includes administering a phosphorylation inhibitor or a dephosphorylation agent against phosphorylation of:
- a tyrosine residue(s) at the 111-th position and/or the 249-th position of human IDO1; or
- a tyrosine residue(s) of non-human IDO1 at a position(s) corresponding to the 111-th position and/or the 249-th position of human IDO1 to a solid tumor comprising a tumor cell in which said human IDO1 or non-human IDO1 tyrosine residue(s) is/are phosphorylated or a subject who carries a solid tumor comprising the tumor cell,
- wherein the phosphorylation inhibitor or the dephosphorylation agent is a Src inhibitor selected from a group consisting of dasatinib, bosutinib, saracatinib, ponatinib, ilorasertib, N-benzyl-2-(5-(4-(2-morpholinoethoxy)phenyl)pyridin-2-yl)acetamide, 4-amino-5-(4-chlorophenyl)-7-(tert-butyl)pyrazolo-[3,4-d]pyrimidine, 4-amino-5-(4-methylphenyl)-7-(tert-butyl)pyrazolo-[3,4-d]pyrimidine, 4-(4'-phenoxyanilino)-6,7-dimethoxyquinazoline, 2-((3,5-di-tert-Butyl-4-hydroxyphenyl)-methylene)-4-cyclopentene-1,3-dione, 4-N-(5-cyclopropyl-1H-pyrazol-3-yl)-6-(4-methylpiperazin-1-yl)-2-N-[(3-propan-2-yl-1,2-oxazol-5-yl)methyl]yrimidine-2,4-diamine, [7-(2,6-dichloro-phenyl)-5-methyl-benzo[1,2,4]triazin-3-yl]-[4-(2-pyrrolidin-1-yl-ethoxy)-phenyl]-amine, [7-(2,6-dichloro-phenyl)-5-methyl-benzo[1,2,4]triazin-3-yl]-{4-[2-(1-oxy-pyrrolidin-1-yl)-ethoxy]-phenyl}-amine, and rebastinib, and salts, hydrates, and solvates thereof, and
- wherein the method is used in combination with a therapy for the purpose of removing immunosuppression caused by cancer.

4. The method according to claim 3, wherein the therapy includes administering anti-PD-1 antibody or anti-PD-L1 antibody to the the tumor cell or the subject.

5. The method according to claim 1, further comprising: prior to the administering, detecting, in a tumor cell obtained from the subject, the phosphorylation of: a tyrosine residue(s) at the 111-th position and/or the 249-th position of human IDO1; or a tyrosine residue(s) of non-human IDO1 at a position(s) corresponding to the 111-th position and/or the 249-th position of human IDO1.

6. The method according to claim 5, wherein the detecting includes using an antibody to detect, in a tumor cell obtained from the subject, phosphorylation of:
- a tyrosine residue(s) at the 111-th position and/or the 249-th position of human IDO1; or
- a tyrosine residue(s) of non-human IDO1 at a position(s) corresponding to the 111-th position and/or the 249-th position of human IDO1.

7. A method for inhibiting the growth and/or invasion of a tumor cell in which a tyrosine residue(s) at the 111-th position and/or the 249-th position of human IDO1, or a tyrosine residue(s) of non-human IDO1 at a position(s) corresponding to the 111-th position and/or the 249-th position of human IDO1 is/are phosphorylated, including administering a Src inhibitor to the tumor cell or a subject who carries the tumor cell and further administering a drug to the tumor cell or the subject for the purpose of removing immunosuppression caused by cancer,
wherein the Src inhibitor is selected from a group consisting of dasatinib, bosutinib, saracatinib, ponatinib, ilorasertib, N-benzyl-2-(5-(4-(2-morpholinoethoxy)phenyl)pyridin-2-yl)acetamide, 4-amino-5-(4-chlorophenyl)-7-(tert-butyl)pyrazolo-[3,4-d]pyrimidine, 4-amino-5-(4-methylphenyl)-7-(tert-butyl)pyrazolo-[3,4-d]pyrimidine, 4-(4'-phenoxyanilino)-6,7-dimethoxyquinazoline, 2-((3,5-di-tert-Butyl-4-hydroxyphenyl)-methylene)-4-cyclopentene-1,3-dione, 4-N-(5-cyclopropyl-1H-pyrazol-3-yl)-6-(4-methylpiperazin-1-yl)-2-N-[(3-propan-2-yl-1,2-oxazol-5-yl)methyl]pyrimidine-2,4-diamine, [7-(2,6-dichloro-phenyl)-5-methyl-benzo[1,2,4]triazin-3-yl]-[4-(2-pyrrolidin-1-yl-ethoxy)-phenyl]-amine, [7-(2,6-dichloro-phenyl)-5-methyl-benzo[1,2,4]triazin-3-yl]-{4-[2-(1-oxy-pyrrolidin-1-yl)-ethoxy]-phenyl}-amine, and rebastinib, and salts, hydrates, and solvates thereof, and wherein the tumor cell is from a solid tumor.

8. A method for inhibiting the growth and/or invasion of a tumor cell in which a tyrosine residue(s) at the 111-th position and/or the 249-th position of human IDO1, or a tyrosine residue(s) of non-human IDO1 at a position(s) corresponding to the 111-th position and/or the 249-th position of human IDO1 is/are phosphorylated, including administering a Src inhibitor to the tumor cell or a subject who carries the tumor cell, wherein the method is used in combination with a therapy for the purpose of removing immunosuppression caused by cancer,
wherein the Src inhibitor is selected from a group consisting of dasatinib, bosutinib, saracatinib, ponatinib, ilorasertib, N-benzyl-2-(5-(4-(2-morpholinoethoxy)phenyl)pyridin-2-yl)acetamide, 4-amino-5-(4-chlorophenyl)-7-(tert-butyl)pyrazolo-[3,4-d]pyrimidine, 4-amino-5-(4-methylphenyl)-7-(tert-butyl)pyrazolo-[3,4-d]pyrimidine, 4(4'-phenoxyanilino)-6,7-dimethoxyquinazoline, 2-((3,5-di-tert-Butyl-4-hydroxyphenyl)-methylene)-4-cyclopentene-1,3-dione, 4-N-(5-cyclopropyl-1H-pyrazol-3-yl)-6-(4-methylpiperazin-1-yl)-2-N-[(3-propan-2-yl-1,2-oxazol-5-yl)methyl]pyrimidine-2,4-diamine, [7-(2,6-dichloro-phenyl)-5-methyl-benzo[1,2,4]triazin-3-yl]-[4-(2-pyrrolidin-1-yl-ethoxy)-phenyl]-amine, [7-(2,6-dichloro-phenyl)-5-methyl-benzo[1,2,4]triazin-3-yl]-{4-[2-(1-oxy-pyrrolidin-1-yl)-ethoxy]-phenyl}-amine, and rebastinib, and salts, hydrates, and solvates thereof, and wherein the tumor cell is from a solid tumor.

9. The method according to claim 7, wherein the drug includes anti-PD-1 antibody or anti-PD-L1 antibody.

10. The method according to claim 8, wherein the therapy includes administering anti-PD-1 antibody or anti-PD-L1 antibody to the tumor cell or the subject.

* * * * *

SEQUENCE LISTING

```
<160> NUMBER OF SEQ ID NOS: 19

<210> SEQ ID NO 1
<211> LENGTH: 403
<212> TYPE: PRT
<213> ORGANISM: Human IDO1

<400> SEQUENCE: 1

Met Ala His Ala Met Glu Asn Ser Trp Thr Ile Ser Lys Glu Tyr His
1               5                   10                  15

Ile Asp Glu Glu Val Gly Phe Ala Leu Pro Asn Pro Gln Glu Asn Leu
            20                  25                  30

Pro Asp Phe Tyr Asn Asp Trp Met Phe Ile Ala Lys His Leu Pro Asp
        35                  40                  45

Leu Ile Glu Ser Gly Gln Leu Arg Glu Arg Val Glu Lys Leu Asn Met
    50                  55                  60

Leu Ser Ile Asp His Leu Thr Asp His Lys Ser Gln Arg Leu Ala Arg
65                  70                  75                  80

Leu Val Leu Gly Cys Ile Thr Met Ala Tyr Val Trp Gly Lys Gly His
                85                  90                  95

Gly Asp Val Arg Lys Val Leu Pro Arg Asn Ile Ala Val Pro Tyr Cys
            100                 105                 110

Gln Leu Ser Lys Lys Leu Glu Leu Pro Pro Ile Leu Val Tyr Ala Asp
        115                 120                 125

Cys Val Leu Ala Asn Trp Lys Lys Lys Asp Pro Asn Lys Pro Leu Thr
    130                 135                 140

Tyr Glu Asn Met Asp Val Leu Phe Ser Phe Arg Asp Gly Asp Cys Ser
145                 150                 155                 160

Lys Gly Phe Phe Leu Val Ser Leu Leu Val Glu Ile Ala Ala Ala Ser
                165                 170                 175

Ala Ile Lys Val Ile Pro Thr Val Phe Lys Ala Met Gln Met Gln Glu
            180                 185                 190

Arg Asp Thr Leu Leu Lys Ala Leu Leu Glu Ile Ala Ser Cys Leu Glu
        195                 200                 205

Lys Ala Leu Gln Val Phe His Gln Ile His Asp His Val Asn Pro Lys
    210                 215                 220

Ala Phe Phe Ser Val Leu Arg Ile Tyr Leu Ser Gly Trp Lys Gly Asn
225                 230                 235                 240

Pro Gln Leu Ser Asp Gly Leu Val Tyr Glu Gly Phe Trp Glu Asp Pro
                245                 250                 255

Lys Glu Phe Ala Gly Gly Ser Ala Gly Gln Ser Ser Val Phe Gln Cys
            260                 265                 270
```

```
Phe Asp Val Leu Leu Gly Ile Gln Gln Thr Ala Gly Gly His Ala
            275                 280                 285

Ala Gln Phe Leu Gln Asp Met Arg Arg Tyr Met Pro Pro Ala His Arg
    290                 295                 300

Asn Phe Leu Cys Ser Leu Glu Ser Asn Pro Ser Val Arg Glu Phe Val
305                 310                 315                 320

Leu Ser Lys Gly Asp Ala Gly Leu Arg Glu Ala Tyr Asp Ala Cys Val
                325                 330                 335

Lys Ala Leu Val Ser Leu Arg Ser Tyr His Leu Gln Ile Val Thr Lys
                340                 345                 350

Tyr Ile Leu Ile Pro Ala Ser Gln Gln Pro Lys Glu Asn Lys Thr Ser
                355                 360                 365

Glu Asp Pro Ser Lys Leu Glu Ala Lys Gly Thr Gly Gly Thr Asp Leu
    370                 375                 380

Met Asn Phe Leu Lys Thr Val Arg Ser Thr Thr Glu Lys Ser Leu Leu
385                 390                 395                 400

Lys Glu Gly

<210> SEQ ID NO 2
<211> LENGTH: 407
<212> TYPE: PRT
<213> ORGANISM: Mouse IDO1

<400> SEQUENCE: 2

Met Ala Leu Ser Lys Ile Ser Pro Thr Glu Gly Ser Arg Arg Ile Leu
1               5                   10                  15

Glu Asp His His Ile Asp Glu Asp Val Gly Phe Ala Leu Pro His Pro
                20                  25                  30

Leu Val Glu Leu Pro Asp Ala Tyr Ser Pro Trp Val Leu Val Ala Arg
            35                  40                  45

Asn Leu Pro Val Leu Ile Glu Asn Gly Gln Leu Arg Glu Glu Val Glu
    50                  55                  60

Lys Leu Pro Thr Leu Ser Thr Asp Gly Leu Arg Gly His Arg Leu Gln
65                  70                  75                  80

Arg Leu Ala His Leu Ala Leu Gly Tyr Ile Thr Met Ala Tyr Val Trp
                85                  90                  95

Asn Arg Gly Asp Asp Asp Val Arg Lys Val Leu Pro Arg Asn Ile Ala
                100                 105                 110

Val Pro Tyr Cys Glu Leu Ser Glu Lys Leu Gly Leu Pro Pro Ile Leu
            115                 120                 125

Ser Tyr Ala Asp Cys Val Leu Ala Asn Trp Lys Lys Lys Asp Pro Asn
    130                 135                 140

Gly Pro Met Thr Tyr Glu Asn Met Asp Ile Leu Phe Ser Phe Pro Gly
145                 150                 155                 160

Gly Asp Cys Asp Lys Gly Phe Phe Leu Val Ser Leu Leu Val Glu Ile
                165                 170                 175

Ala Ala Ser Pro Ala Ile Lys Ala Ile Pro Thr Val Ser Ser Ala Val
                180                 185                 190

Glu Arg Gln Asp Leu Lys Ala Leu Glu Lys Ala Leu His Asp Ile Ala
            195                 200                 205

Thr Ser Leu Glu Lys Ala Lys Glu Ile Phe Lys Arg Met Arg Asp Phe
    210                 215                 220

Val Asp Pro Asp Thr Phe Phe His Val Leu Arg Ile Tyr Leu Ser Gly
225                 230                 235                 240
```

-continued

```
Trp Lys Cys Ser Ser Lys Leu Pro Glu Gly Leu Leu Tyr Glu Gly Val
            245                 250                 255

Trp Asp Thr Pro Lys Met Phe Ser Gly Ser Ala Gly Gln Ser Ser
        260                 265                 270

Ile Phe Gln Ser Leu Asp Val Leu Gly Ile Lys His Glu Ala Gly
            275                 280                 285

Lys Glu Ser Pro Ala Glu Phe Leu Gln Glu Met Arg Glu Tyr Met Pro
        290                 295                 300

Pro Ala His Arg Asn Phe Leu Phe Leu Glu Ser Ala Pro Pro Val
305                 310                 315                 320

Arg Glu Phe Val Ile Ser Arg His Asn Glu Asp Leu Thr Lys Ala Tyr
                325                 330                 335

Asn Glu Cys Val Asn Gly Leu Val Ser Val Arg Lys Phe His Leu Ala
            340                 345                 350

Ile Val Asp Thr Tyr Ile Met Lys Pro Ser Lys Lys Pro Thr Asp
            355                 360                 365

Gly Asp Lys Ser Glu Glu Pro Ser Asn Val Glu Ser Arg Gly Thr Gly
        370                 375                 380

Gly Thr Asn Pro Met Thr Phe Leu Arg Ser Val Lys Asp Thr Thr Glu
385                 390                 395                 400

Lys Ala Leu Leu Ser Trp Pro
                405

<210> SEQ ID NO 3
<211> LENGTH: 268
<212> TYPE: PRT
<213> ORGANISM: Human Slug

<400> SEQUENCE: 3

Met Pro Arg Ser Phe Leu Val Lys Lys His Phe Asn Ala Ser Lys Lys
1               5                   10                  15

Pro Asn Tyr Ser Glu Leu Asp Thr His Thr Val Ile Ile Ser Pro Tyr
            20                  25                  30

Leu Tyr Glu Ser Tyr Ser Met Pro Val Ile Pro Gln Pro Glu Ile Leu
        35                  40                  45

Ser Ser Gly Ala Tyr Ser Pro Ile Thr Val Trp Thr Thr Ala Ala Pro
    50                  55                  60

Phe His Ala Gln Leu Pro Asn Gly Leu Ser Pro Leu Ser Gly Tyr Ser
65                  70                  75                  80

Ser Ser Leu Gly Arg Val Ser Pro Pro Pro Ser Asp Thr Ser Ser
            85                  90                  95

Lys Asp His Ser Gly Ser Glu Ser Pro Ile Ser Asp Glu Glu Arg
        100                 105                 110

Leu Gln Ser Lys Leu Ser Asp Pro His Ala Ile Glu Ala Glu Lys Phe
    115                 120                 125

Gln Cys Asn Leu Cys Asn Lys Thr Tyr Ser Thr Phe Ser Gly Leu Ala
    130                 135                 140

Lys His Lys Gln Leu His Cys Asp Ala Gln Ser Arg Lys Ser Phe Ser
145                 150                 155                 160

Cys Lys Tyr Cys Asp Lys Glu Tyr Val Ser Leu Gly Ala Leu Lys Met
                165                 170                 175

His Ile Arg Thr His Thr Leu Pro Cys Val Cys Lys Ile Cys Gly Lys
            180                 185                 190

Ala Phe Ser Arg Pro Trp Leu Leu Gln Gly His Ile Arg Thr His Thr
```

```
                195                 200                 205
Gly Glu Lys Pro Phe Ser Cys Pro His Cys Asn Arg Ala Phe Ala Asp
            210                 215                 220

Arg Ser Asn Leu Arg Ala His Leu Gln Thr His Ser Asp Val Lys Lys
225                 230                 235                 240

Tyr Gln Cys Lys Asn Cys Ser Lys Thr Phe Ser Arg Met Ser Leu Leu
                245                 250                 255

His Lys His Glu Glu Ser Gly Cys Cys Val Ala His
            260                 265

<210> SEQ ID NO 4
<211> LENGTH: 269
<212> TYPE: PRT
<213> ORGANISM: Mouse Slug

<400> SEQUENCE: 4

Met Pro Arg Ser Phe Leu Val Lys Lys His Phe Asn Ala Ser Lys Lys
1               5                  10                  15

Pro Asn Tyr Ser Glu Leu Asp Thr His Thr Val Ile Ile Ser Pro Tyr
            20                  25                  30

Leu Tyr Glu Ser Tyr Pro Ile Pro Val Ile Pro Lys Pro Glu Ile Leu
        35                  40                  45

Thr Ser Gly Ala Tyr Ser Pro Ile Thr Val Trp Thr Ser Ser Ala Ala
    50                  55                  60

Pro Leu His Ser Pro Leu Pro Ser Gly Leu Ser Pro Leu Thr Gly Tyr
65                  70                  75                  80

Ser Ser Ser Leu Gly Arg Val Ser Pro Pro Ser Ser Asp Thr Ser
                85                  90                  95

Ser Lys Asp His Ser Gly Ser Glu Ser Pro Ile Ser Asp Glu Glu Glu
            100                 105                 110

Arg Leu Gln Pro Lys Leu Ser Asp Pro His Ala Ile Glu Ala Glu Lys
        115                 120                 125

Phe Gln Cys Asn Leu Cys Asn Lys Thr Tyr Ser Thr Phe Ser Gly Leu
    130                 135                 140

Ala Lys His Lys Gln Leu His Cys Asp Ala Gln Ser Arg Lys Ser Phe
145                 150                 155                 160

Ser Cys Lys Tyr Cys Asp Lys Glu Tyr Val Ser Leu Gly Ala Leu Lys
                165                 170                 175

Met His Ile Arg Thr His Thr Leu Pro Cys Val Cys Lys Ile Cys Gly
            180                 185                 190

Lys Ala Phe Ser Arg Pro Trp Leu Leu Gln Gly His Ile Arg Thr His
        195                 200                 205

Thr Gly Glu Lys Pro Phe Ser Cys Pro His Cys Asn Arg Ala Phe Ala
    210                 215                 220

Asp Arg Ser Asn Leu Arg Ala His Leu Gln Thr His Ser Asp Val Lys
225                 230                 235                 240

Lys Tyr Gln Cys Lys Asn Cys Ser Lys Thr Phe Ser Arg Met Ser Leu
                245                 250                 255

Leu His Lys His Glu Glu Ser Gly Cys Cys Val Ala His
            260                 265

<210> SEQ ID NO 5
<211> LENGTH: 8
<212> TYPE: PRT
<213> ORGANISM: Artificial Sequence
<220> FEATURE:
```

<223> OTHER INFORMATION: gp70 H-2Kb-restricted epitope peptide

<400> SEQUENCE: 5

Lys Ser Pro Trp Phe Thr Thr Leu
1               5

<210> SEQ ID NO 6
<211> LENGTH: 8
<212> TYPE: PRT
<213> ORGANISM: Artificial Sequence
<220> FEATURE:
<223> OTHER INFORMATION: beta-gal H-2Kb-restricted epitope peptide

<400> SEQUENCE: 6

Asp Ala Pro Ile Tyr Thr Asn Val
1               5

<210> SEQ ID NO 7
<211> LENGTH: 20
<212> TYPE: PRT
<213> ORGANISM: Artificial Sequence
<220> FEATURE:
<223> OTHER INFORMATION: Surrounding sequence for IDO1 pTyr249
<220> FEATURE:
<221> NAME/KEY: MOD_RES
<222> LOCATION: (5)..(5)
<223> OTHER INFORMATION: PHOSPHORYLATION

<400> SEQUENCE: 7

Asp Gly Leu Val Tyr Glu Gly Phe Trp Glu Asp Pro Lys Glu Phe Ala
1               5                   10                  15

Gly Gly Ser Cys
            20

<210> SEQ ID NO 8
<211> LENGTH: 22
<212> TYPE: DNA
<213> ORGANISM: Artificial Sequence
<220> FEATURE:
<223> OTHER INFORMATION: Primer for mSlug

<400> SEQUENCE: 8
ttacccagtg gcctttctcc tc                                           22

<210> SEQ ID NO 9
<211> LENGTH: 22
<212> TYPE: DNA
<213> ORGANISM: Artificial Sequence
<220> FEATURE:
<223> OTHER INFORMATION: Primer for mSlug

<400> SEQUENCE: 9
ggttcgaatg tgcatcttca gg                                           22

<210> SEQ ID NO 10
<211> LENGTH: 22
<212> TYPE: DNA
<213> ORGANISM: Artificial Sequence
<220> FEATURE:
<223> OTHER INFORMATION: Primer for mCyp1a1

<400> SEQUENCE: 10
ggttggccac tttgaccctt ac                                           22

<210> SEQ ID NO 11
<211> LENGTH: 22

```
<212> TYPE: DNA
<213> ORGANISM: Artificial Sequence
<220> FEATURE:
<223> OTHER INFORMATION: Primer for mCyp1a1

<400> SEQUENCE: 11
aacctcccca aactcattgc tc                                              22

<210> SEQ ID NO 12
<211> LENGTH: 22
<212> TYPE: DNA
<213> ORGANISM: Artificial Sequence
<220> FEATURE:
<223> OTHER INFORMATION: Primer for mGAPDH

<400> SEQUENCE: 12
catgacaact ttggcattgt gg                                              22

<210> SEQ ID NO 13
<211> LENGTH: 22
<212> TYPE: DNA
<213> ORGANISM: Artificial Sequence
<220> FEATURE:
<223> OTHER INFORMATION: Primer for mGAPDH

<400> SEQUENCE: 13
gtccaccacc ctgttgctgt ag                                              22

<210> SEQ ID NO 14
<211> LENGTH: 21
<212> TYPE: DNA
<213> ORGANISM: Artificial Sequence
<220> FEATURE:
<223> OTHER INFORMATION: Target sequence for shRNA

<400> SEQUENCE: 14
gcagacccac tctgatgtaa a                                               21

<210> SEQ ID NO 15
<211> LENGTH: 21
<212> TYPE: DNA
<213> ORGANISM: Artificial Sequence
<220> FEATURE:
<223> OTHER INFORMATION: non-specific sequence as negative control

<400> SEQUENCE: 15
caacaagatg aagagcacca a                                               21

<210> SEQ ID NO 16
<211> LENGTH: 22
<212> TYPE: DNA
<213> ORGANISM: Artificial Sequence
<220> FEATURE:
<223> OTHER INFORMATION: Primer for hSlug

<400> SEQUENCE: 16
actgtgtgga ctaccgctgc tc                                              22

<210> SEQ ID NO 17
<211> LENGTH: 22
<212> TYPE: DNA
<213> ORGANISM: Artificial Sequence
<220> FEATURE:
<223> OTHER INFORMATION: Primer for hSlug

<400> SEQUENCE: 17
```

```
ccccgtgtg agttctaatg tg                                            22

<210> SEQ ID NO 18
<211> LENGTH: 19
<212> TYPE: DNA
<213> ORGANISM: Artificial Sequence
<220> FEATURE:
<223> OTHER INFORMATION: Primer for hGAPDH

<400> SEQUENCE: 18
tgaacgggaa gctcactgg                                               19

<210> SEQ ID NO 19
<211> LENGTH: 20
<212> TYPE: DNA
<213> ORGANISM: Artificial Sequence
<220> FEATURE:
<223> OTHER INFORMATION: Primer for hGAPDH

<400> SEQUENCE: 19
tccaccaccc tgttgctgta                                              20
```